US 8,747,341 B2

(12) United States Patent
Farrow et al.

(10) Patent No.: US 8,747,341 B2
(45) Date of Patent: Jun. 10, 2014

(54) SHEET-BASED COMPRESSION GARMENT

(71) Applicant: Farrow Medical Innovations Holdings LLC, Bryan, TX (US)

(72) Inventors: Wade P. Farrow, College Station, TX (US); Barry L. Creighton, College Station, TX (US)

(73) Assignee: Farrow Medical Innovations Holdings LLC, Bryan, TX (US)

(*) Notice: Subject to any disclaimer, the term of this patent is extended or adjusted under 35 U.S.C. 154(b) by 0 days.

(21) Appl. No.: 13/931,582

(22) Filed: Jun. 28, 2013

(65) Prior Publication Data

US 2013/0296763 A1    Nov. 7, 2013

Related U.S. Application Data

(63) Continuation of application No. 13/563,627, filed on Jul. 31, 2012, which is a continuation of application No. 13/239,158, filed on Sep. 21, 2011, now Pat. No. 8,251,933, which is a continuation of application No. 13/108,933, filed on May 16, 2011, now Pat. No. 8,221,340, which is a continuation of application No. 11/733,991, filed on Apr. 11, 2007, now Pat. No. 7,942,838.

(51) Int. Cl.
*A61F 15/00* (2006.01)

(52) U.S. Cl.
USPC .................. 602/75; 602/20; 602/23; 602/60

(58) Field of Classification Search
USPC ............. 602/13, 20, 23, 60–63, 75; 128/882, 128/DIG. 23; 601/46
See application file for complete search history.

(56) References Cited

U.S. PATENT DOCUMENTS 2,687,723 A    8/1954    Stern
2,816,361 A    12/1957   Jobst
(Continued)

FOREIGN PATENT DOCUMENTS

GB    2373444       9/2002
WO    WO 99/36019   7/1999
(Continued)

OTHER PUBLICATIONS

3M Coban 2 Layer Compression System, Commonly Asked Questions, Feb. 13, 2007, pp. 1-3.

(Continued)

*Primary Examiner* — Michael A. Brown
(74) *Attorney, Agent, or Firm* — Warren M. Pate; Pate Peterson, PLLC

(57) ABSTRACT

A compression garment for treating edema is disclosed. The garment may include first and second bands. Each of the bands may comprise a first end, second end opposite the first end, and an intermediate portion located between the first and second ends. The first and second bands may each comprise short-stretch material having a maximum elastic elongation in the range of about 15% up to about 100%. The first band may wrap around a first portion of a patient's limb. The second band may wrap around a second portion of the limb. The first and second bands may be applied such that the intermediate portion of the first band and the intermediate portion of the second band abut without overlapping one another. Once applied, the garment may provide therapeutic compression to the patient's limb.

20 Claims, 13 Drawing Sheets

(56) References Cited

U.S. PATENT DOCUMENTS

| | | | |
|---|---|---|---|
| 3,298,366 | A | 1/1967 | Moore et al. |
| 3,312,219 | A | 4/1967 | Peckham |
| 3,856,008 | A * | 12/1974 | Fowler et al. .................. 602/62 |
| 4,215,687 | A | 8/1980 | Shaw |
| 4,577,622 | A | 3/1986 | Jennings |
| 5,036,838 | A | 8/1991 | Sherman |
| 5,218,954 | A | 6/1993 | van Bemmelen |
| 5,387,183 | A | 2/1995 | Jones |
| 5,520,630 | A | 5/1996 | Daneshvar |
| 5,653,244 | A | 8/1997 | Shaw |
| 5,733,321 | A | 3/1998 | Brink |
| 5,741,220 | A | 4/1998 | Brink |
| 5,897,518 | A | 4/1999 | Shaw |
| 5,906,206 | A | 5/1999 | Shaw et al. |
| 5,918,602 | A | 7/1999 | Shaw et al. |
| 5,993,405 | A | 11/1999 | Wynn |
| 6,109,267 | A | 8/2000 | Shaw et al. |
| 6,123,681 | A | 9/2000 | Brown, III |
| 6,125,681 | A * | 10/2000 | Orcutt et al. .................. 72/402 |
| 6,152,893 | A | 11/2000 | Pigg et al. |
| 6,254,554 | B1 * | 7/2001 | Turtzo .................. 601/134 |
| 6,338,723 | B1 | 1/2002 | Carpenter et al. |
| 6,415,525 | B1 | 7/2002 | Watkins |
| 6,617,485 | B2 | 9/2003 | Herzberg |
| 6,860,862 | B2 | 3/2005 | Waldridge et al. |
| 7,135,007 | B2 | 11/2006 | Scott et al. |
| 7,173,161 | B1 | 2/2007 | Kandt |
| 7,329,232 | B2 | 2/2008 | Lipshaw et al. |
| 7,513,881 | B1 | 4/2009 | Grim et al. |
| 7,867,185 | B2 | 1/2011 | Lipshaw |
| 7,942,838 | B2 | 5/2011 | Farrow |
| 8,221,340 | B2 | 7/2012 | Farrow |
| 8,251,933 | B2 | 8/2012 | Farrow |
| 8,376,977 | B2 | 2/2013 | Farrow |
| 8,491,514 | B2 | 7/2013 | Farrow et al. |
| 8,529,483 | B2 | 9/2013 | Farrow |
| 2002/0022791 | A1 * | 2/2002 | Morris et al. .................. 601/149 |
| 2003/0149389 | A1 | 8/2003 | Daneshvar |
| 2005/0113729 | A1 | 5/2005 | Scott et al. |
| 2005/0192524 | A1 | 9/2005 | Lipshaw et al. |
| 2005/0209545 | A1 | 9/2005 | Farrow |
| 2007/0276310 | A1 | 11/2007 | Lipshaw et al. |
| 2007/0282232 | A1 | 12/2007 | Hoffman |
| 2011/0125183 | A1 | 5/2011 | Lipshaw et al. |
| 2012/0179084 | A1 | 7/2012 | Lipshaw et al. |

FOREIGN PATENT DOCUMENTS

| | | |
|---|---|---|
| WO | WO 00/15139 | 3/2000 |
| WO | WO 2005/092401 | 10/2005 |
| WO | WO 2008/127929 | 10/2008 |

OTHER PUBLICATIONS

3M Coban 2 Layer Compression System, Patient Instructions, 2006, 1 page.

New 3M Coban 2 Layer Compression System Introduced for the Treatment of Edema Associated with Venous Leg Ulcers, Press Release, May 1, 2006, pp. 1-3.

Farbifoam Achilles Healer, http://www.fabrifoam.com/p-achilleshealer.html, retrieved Sep. 30, 2005.

Fabrifoam AnkleGard, http://www.fabrifoam.com/p-anklegard.html, retrieved Sep. 30, 2005.

Fabrifoam AnkleWrap, http://www.fabrifoam.com/p-anklewrap.html, retrieved Sep. 30, 2005.

Fabrifoam CarpalGard, http://www.fabrifoam.com/p-carpalgard.html, retrieved Jan. 7, 2010.

Fabrifoam ElbowGard, http://www.fabrifoam.com/p-elbowgard.html, retrieved Jan. 7, 2010.

Fabrifoam KneeGard, http://www.fabrifoam.com/p-kneegard.html, retrieved Sep. 30, 2005.

Fabrifoam MediWrap, http://www.fabrifoam.com/p-mediwrap.html, retrieved Jan. 7, 2010.

Fabrifoam NustimWrap, http://www.fabrifoam.com/p-nustimwrap.html, retrieieved Sep. 30, 2005.

Fabrifoam PattStrap, http://www.fabrifoam.com/p-pattstrap.html, retrieved Jan. 7, 2010.

Fabrifoam ProWrap, http://www.fabrifoam.com/p-prowrap.html, retrieved Sep. 30, 2005.

Fabrifoam Psc, http://www.fabrifoam.com/p-psc.html, retrieved Sep. 30, 2005.

Fabrifoam SuperWrap, http://www.fabrifoam.com/p-superwrap.html, retrieved Sep. 30, 2005.

Fabrifoam WristWrap, http://www.fabrifoam.com/p-wristwrap.html, retrieved Jan. 7, 2010.

Hawkins, a New Cohesive Short-Stretch Bandage and Its Application, British Journal of Nursing, Feb. 22, 2001-Mar. 7, 2001, pp. 249-253.

Lawrance, Use of Velcro Wrap System in the Management of Lower Limb Lymphoedema/Chronic Oedema, Journal of Lymphoedema, 2008, vol. 3, No. 2, pp. 65-70.

Mayrovitz, Compression Therapy: a Summary of Important Concepts and Features, 2004, pp. 1-11.

Medassist Orthotic Products, www.medassistgp.com, 6 pages.

Mosti et al., Compression Therapy in the Treatment of Leg Ulcers, Acia Vulnologica, vol. 7, No. 3, May 2009, pp. 1-20.

3M Coban 2 Layer Compression System Patient Instructions, 2006, 1 page.

International Preliminary Examination Report completed Jul. 24, 2006 for PCT/US2005/09483, pp. 1-7.

International Search Report and Written Opinion of the International Searching Authority mailed Jul. 6, 2005 for PCT/US2005/09483, pp. 1-12.

Supplemental Partial European Search Report completed Mar. 19, 2008 for EP 05 73 1830, pp. 1-7.

International Search Report and Written Opinion of the International Searching Authority mailed Aug. 14, 2008 for PCT/US2008/059707, pp. 1-7.

Thomas et al., an Evaluation of a New Type of Compression Bandaging System, World Wide Wounds, Sep. 2003, pp. 1-15.

Trinity Lymphedema Centers, http://www.trinitylc.com/cmpgarm1.html, 3 pages.

Understanding Compression Therapy, Medical Education Partnership, LTD, 2003, pp. 1-17.

\* cited by examiner

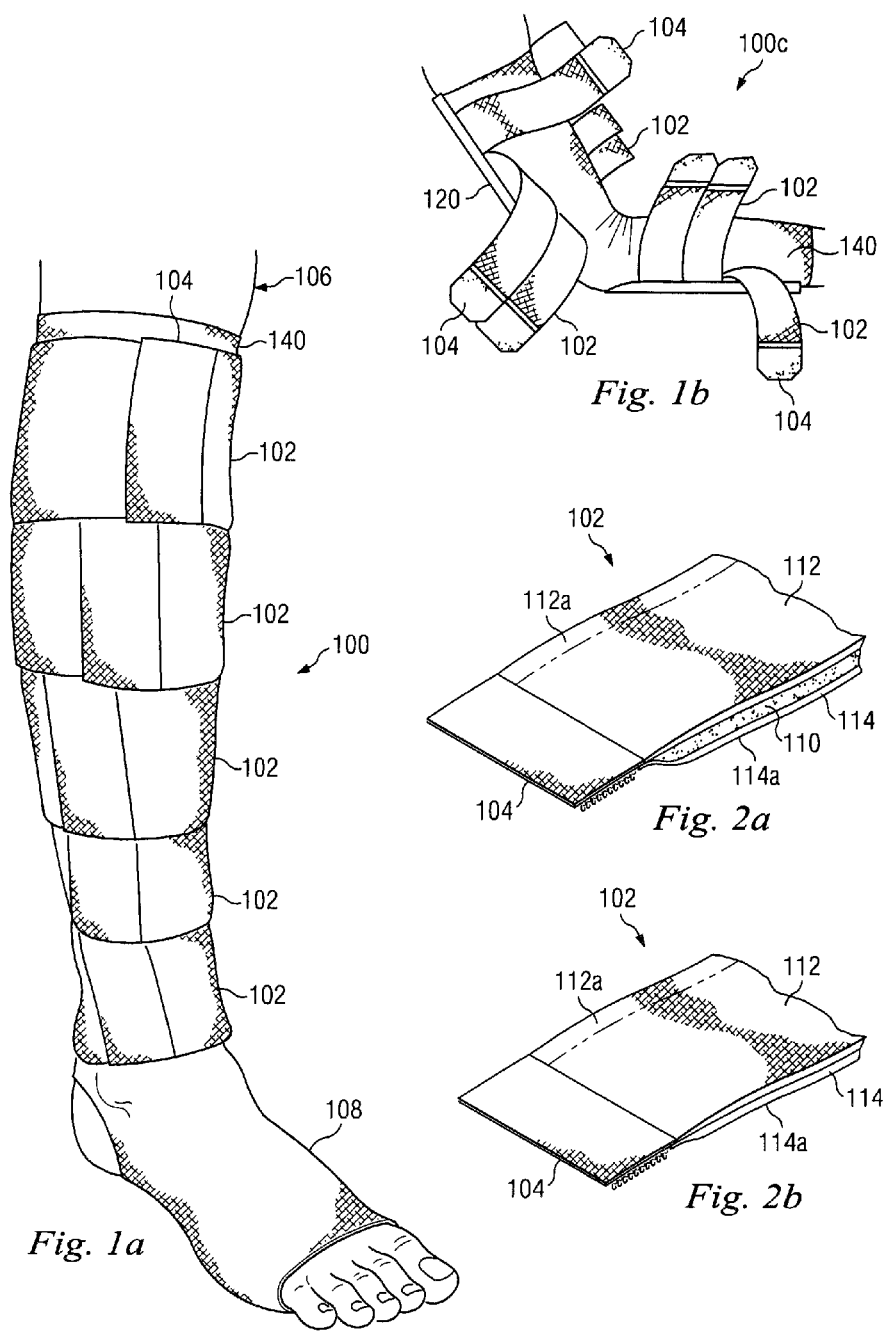

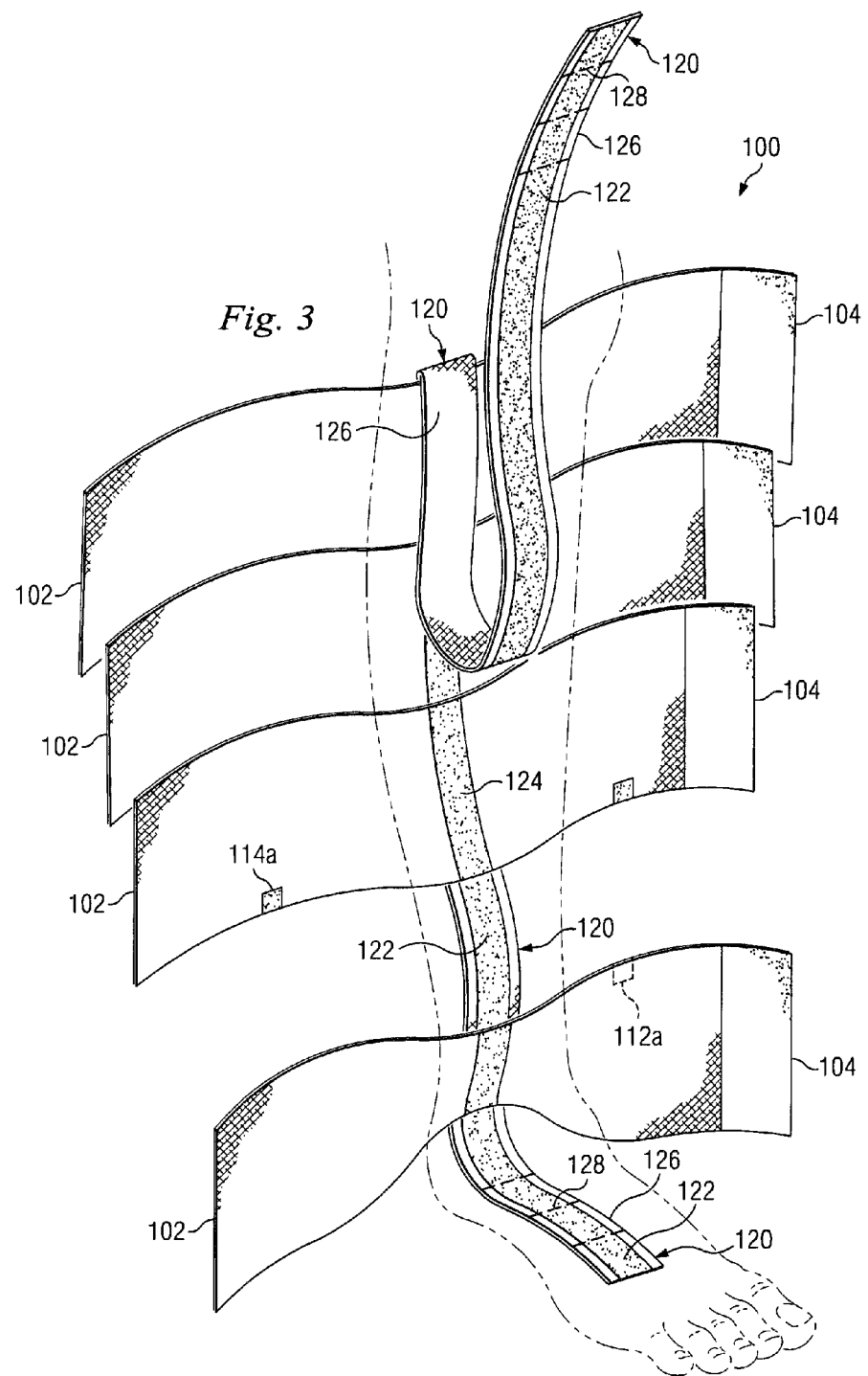

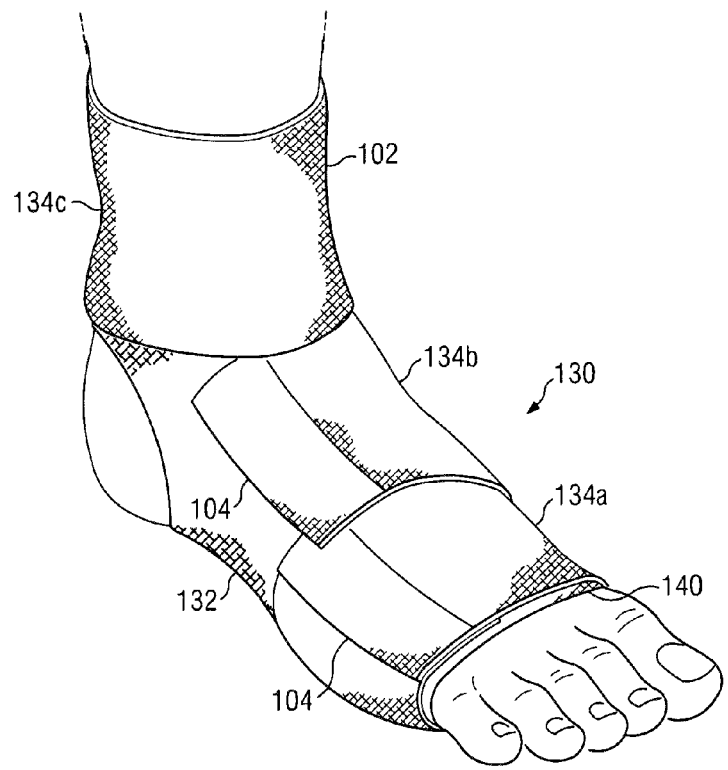
Fig. 6a
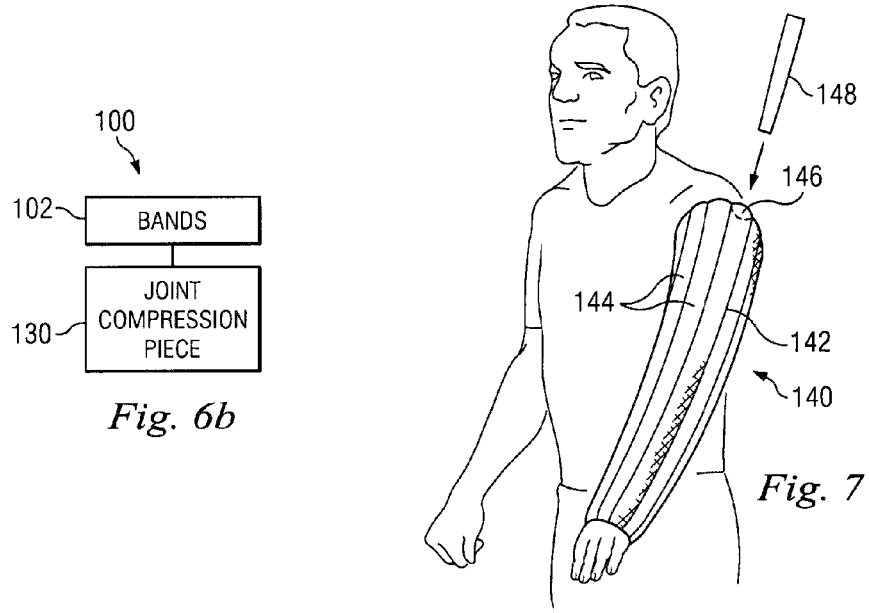
Fig. 6b
Fig. 7

*Fig. 8*

Order Information                                                              200

| Patient Last Name: | | First Name: | |
|---|---|---|---|
| Birth Date: | Sex: M / F | Height: | Weight: |
| Shoe size: | Foot piece type: Anklet / Leg Wrap | | |
| Leg: Right / Left / Both | | | |

202 → (order information block)

Shipping Information

| Contact Person: | | Company: | |
|---|---|---|---|
| Address: | | | |
| City: | | State: | Zip code: |
| Phone Number: | | E-mail: | |

204 → (shipping information block)

Billing Information

206 → Method of Payment: Check / Money Order / Credit Card / Insurance

Device Price:

| Left Leg |
|---|
| 1. Smallest Ankle Circumference (SAC): |
| 2. Circumference 2: |
| 3. Circumference 3: |
| 4. Circumference 4: |
| 5. Circumference 5: |
| 6. Knee crease to SAC: |
| 7. Heel to 5th met head: |
| 8. Midfoot circumference: |

| Right Leg |
|---|
| 1. Smallest Ankle Circumference (SAC): |
| 2. Circumference 2: |
| 3. Circumference 3: |
| 4. Circumference 4: |
| 5. Circumference 5: |
| 6. Knee crease to SAC: |
| 7. Heel to 5th met head: |
| 8. Midfoot circumference: |

208 → (measurements block)

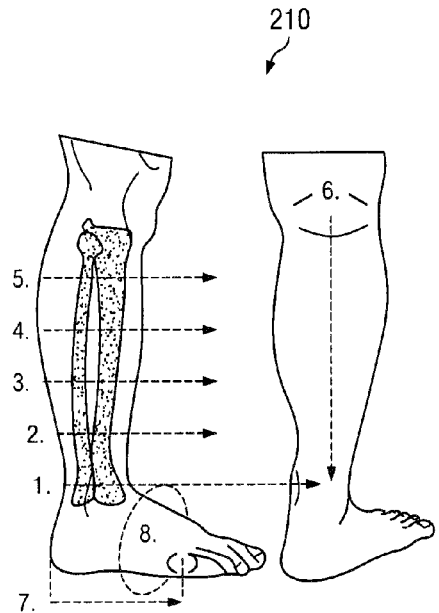

210

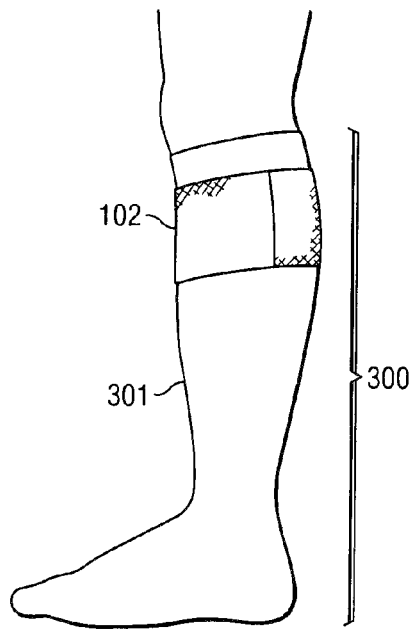
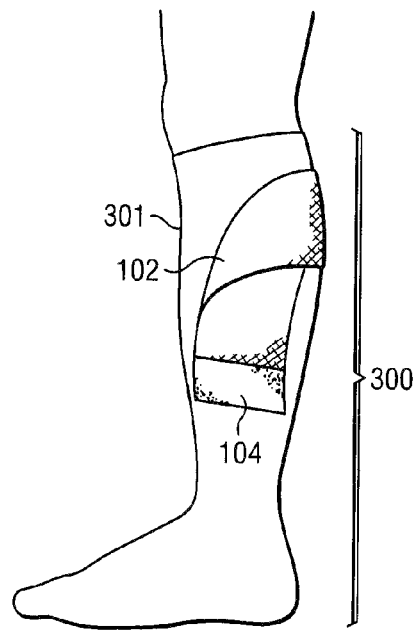
Fig. 12a
Fig. 12b
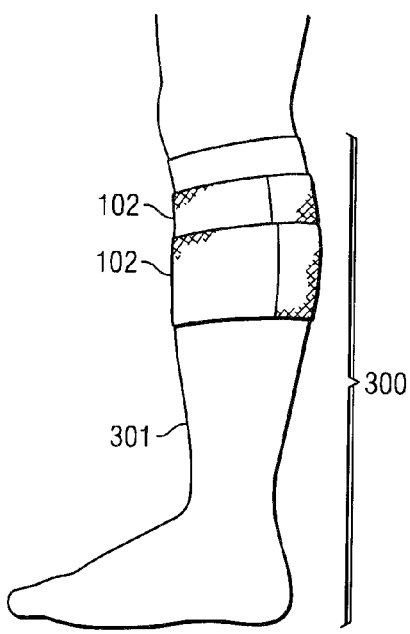
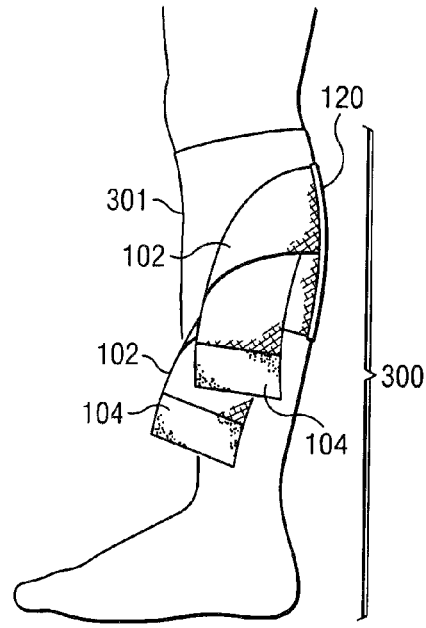
Fig. 12c
Fig. 12d

SHEET-BASED COMPRESSION GARMENT

This application is a continuation of U.S. patent application Ser. No. 13/563,627 filed Jul. 31, 2012, which is a continuation of U.S. patent application Ser. No. 13/239,158 filed Sep. 21, 2011, which is a continuation of U.S. patent application Ser. No. 13/108,933 filed May 16, 2011, which is a continuation of U.S. patent application Ser. No. 11/733,991 filed Apr. 11, 2007.

BACKGROUND

1. Related Applications

U.S. patent application Ser. Nos. 13/563,627, 13/239,158, 13/108,933, 11/733,991, 10/975,590, and U.S. Provisional Patent Application Ser. No. 60/555,150 are each hereby incorporated by reference.

2. Background Art

Excessive interstitial fluid accumulation, referred to as edema, may arise from a variety of illnesses and conditions, including venous valvular insufficiency, postphlebotic syndrome, and lymphedema. Control of this edema by reduction of interstitial fluids is important to increase PO2 delivery to tissues, relieve pain from swelling, and decrease risk of infection. Decreasing drainage of fluid from sores, skin breaks, and/or ulcerations promotes wound closure, and prevents wound breakdown. Compression to an extremity decreases vein diameter and increases flow velocity, which decreases risk of blood clot formation.

Thus, it is desirable to have a customizable or off-the-shelf compressive device that can be readily available for application to a body part to prevent excessive fluid accumulation resulting from a variety of diseases and maladies.

The pathophysiology of venous ulceration is due to hypertension of the venous capillary system. In some cases, this is due to reflux from the venous valvular system, which occurs in older adults. Risk factors include tall height, obesity, inactivity, atherosclerosis, and history of previous deep venous blood clot.

One of the first attempts in treating venous ulceration was made by Paul Gerson Unna, a German pathologist. Dr. Unna invented a zinc paste boot to apply to the leg. This boot provided non-elastic compression to the leg, which augmented the calf-muscle pump to reduce venous hypertension. The Unna boot is still one of the leading methods of treating venous ulcerations today, although the technology has several drawbacks. First, the boot is inflexible. It provides no baseline compression. If applied to an edematous leg, the boot then reduces the edema by augmenting the calf muscle pump, and the limb girth improves. As edema reduces, however, the boot becomes loose on the leg and less effective as the edema reduces. It also loosens the dressing over the ulceration, and may lead to increased drainage and maceration of the peri-wound skin between the ulcer and the boot. Thus, ideally the boot would be able to conform to different size limbs as the edema reduces, maintaining therapeutic compression levels.

Attempts have been made to replace the zinc paste boot with a non-elastic leg binder. These garments are sold under the LegAssist® (Compression Design LLC, Zeeland, Mich.) and Circaid® (Circaid Medical Products Inc., San Diego, Calif.) brands, and use non-elastic bands which interlock around the limb. These garments have adjustable non-elastic bands which use hook and loop material to interconnect the bands. This type of garment has several drawbacks. Many people consider them difficult to don or remove. If the garment is applied on the leg, it does not conform to the limb shape for irregularly shaped limbs as the bands are inelastic. Furthermore, because the bands are inelastic, after the garment is donned the garment becomes loose as the edema reduces, and the garment tends to become loose and fall down. Furthermore, because the bands are inelastic, there is no simple, reliable system for a patient to tell how tight the bands are applied. Attempts to design a garment with elastic bands is also not simple. First, there is the risk the garment will be applied with too much compression and cut off circulation to the limb. Secondly, it is more important for an elastic system to have a simple reliable way to measure the pressure the band applies so dangerous compression levels are not applied.

Another attempt to replace the zinc paste boot is the short-stretch wrap. Sold under the LoPress® (Hartmann Conco Inc., Rock Hill, S.C.) name and the Comprilan® (Jobst, Charlotte, N.C.) brands, these wraps have short-stretch elasticity with low resting compression. These wraps are designed to be applied at maximal stretch. These wraps are particularly useful for lymphedema, although they also work well for venous insufficiency and other types of edema as well. In the case of lymphedema, we find that the active compression level augments the lymphangion micropump in the lymphatic system to augment lymphatic flow. The short-stretch wrap is applied at maximal stretch, so it does a good job augmenting the calf muscle pump to improve venous return. For severe venous ulcerations, they sometimes need higher levels of resting compression.

Traditional compression stockings can provide different ranges of compression that can augment calf muscle pump action. Because the stockings have to fit a range of limb girth, actual compression varies with the range. Also, fluctuations in edema within a single patient and diurnal variations during the course of the day also affect limb girth. This can make the stockings difficult, if not impossible, to don and doff. While compression stockings augment calf muscle function, they are still elastic and therefore the augmentation of the calf muscle pump is not as great as it could be. Patients often purchase weak compression range stockings because they are easier to don, only to find that the limb swells and then the patient cannot don them at all. Also, since compression stockings are made in a circular weave to fit a limited range of limb girth, they loosen as limb edema reduces. Thus, many compression experts recommend using other compression modalities to reduce edema, and then use compression stockings to prevent edema recurrence.

Thus, it would be beneficial to provide a garment that had the ability to maximally augment venous return with calf muscle activation, which also provided active compression to augment the lymphangion micropump system. Furthermore, because edema fluctuates diurnally, it would be beneficial to provide a garment that is adjustable to limb girth so that it is always applied with uniform compression. In addition, it is beneficial to provide active compression so that the garment would not loosen and slip down if limb girth decreases, and the garment would be form fitting since it had some stretch to fit around abnormally shaped limbs. An additional optimal design would be that the user could easily don the garment and get consistent levels of compression with the garment application.

SUMMARY

The present invention provides many different embodiments of a modular compression garment and method of assembly. Listed below are some of the embodiments herein disclosed, it being understood that different embodiments have different features and/or elements, and that no one particular feature or element is considered essential for all embodiments. The following summary also provides various examples of elasticity, compression, and so forth. These are, of course, only meant to be examples and not limitations to the claims.

In some embodiments, a hook and loop garment with active compression that still has non-elastic compression on the calf muscle pump is provided. The garment provides a plurality of bands with short-stretch elasticity (maximum elasticity in the range of 15-100%). Each band is designed to provide a pre-determined level of compression at maximal stretch. This resting compression level can be different for different versions of the garment, e.g., 8-15 mm, 15-20 mm, 20-30 mm, 30-40 mm, or 40-50 mm. Thus, when a band is stretched to its maximum stretch, this predetermined resting level of compression will be reached.

A user can stretch the band and see and/or feel when the maximal stretch level is reached because the band may have a limited stretch range. Using this, the user can 'dial into' the correct level of compression when applying the garment, without needing to use a pressure sensor or an indices-type system to determine the correct compression level. This provides a very simple, but very reliable, method of reproducing the correct level of compression every time the garment is donned. Because the bands are applied at maximal stretch, it will not stretch further. Therefore, the garment provides maximal augmentation of the calf muscle pump and the more the leg tries to swell, the more the garment will work to prevent swelling.

The garment can be designed to be a single use disposable device, or can be designed to be reusable. For severe venous ulcerations with lots of drainage or bioburden, the garment can be designed to be of disposable materials similar to those used in multilayer compression wraps. For mild draining ulcerations, the garment can be designed to be re-usable. In some embodiments, the garment can be used to heal the ulceration, and then the user can continue using the garment for maintenance compression in order to prevent recurrence.

The garment can also be designed to provide graduated compression. For a typical 30-40 mmHg compression stocking, for example, there can be 30-40 mm compression at the ankle, but perhaps 20-30 mm at the calf level, 15-20 mm in the distal thigh, and 8-15 mm in the proximal thigh. Graduated compression provides more compression distally on the limb than proximally, and compensates for gravity to provide optimum compression levels. Different embodiments of the garment can include one of the features listed below to provide a garment with graduated compression. The features listed below can also be mixed and matched to provide graduated compression by combining these various modalities in combination to provide a sophisticated garment with various compression levels:

1) The garment utilizes bands engineered with different levels of compression. For example, all the bands will be designed to have maximal stretch at some short-stretch range (for example 50% maximum extension). The bands around the ankle will be designed to have 40 mm compression at maximal stretch (50% extension). The bands used higher in the garment will be selected to have compression of 30 mm at maximal stretch (50% extension). The bands selected for the thigh portion will have 15 mm compression at maximal stretch (50% extension). The user will apply each band at maximal stretch, and thus have a graduated compression garment which has each band maximally stretched and will thus maximally augment calf muscle pump action and lymphatic function. Since the stretch stops abruptly as the patients stretches the compression band, the patient can easily "dial into" the correct compression level for each band, without the use of complicated modalities such as measuring systems, pressure sensors, or graphic renditions printed on the bands.

2) The garment utilizes bands arranged with different amounts of overlap, e.g., overlap the bands on top of one another more distally than proximally. By overlapping the bands, there is additional compression. For example, if two layers are used distally at the ankle, there will be approximately double the level of compression. For example, in one embodiment using two layers at the ankle may yield 30 mm compression, while a single layer band near the top of the calf may yield 15 mm compression. By varying the degree of overlap, graduated compression can be created when the garment is applied to the limb.

3) The garment utilizes bands of differing lengths. By wrapping the distal band two times around itself, approximately twice the compression is achieved, as compared to a single layer. Thus, using a single band wrapped twice around the ankle would provide about twice the compression level. Similarly, using a single layer around the calf would provide about half as much compression as the one around the ankle. Thus, by varying band length graduated compression can be provided when the garment is applied to the limb.

4) The garment utilizes bands of differing widths. If two bands are applied with the same tension, but one band has ½ the width as the other band, this narrower band would provide about twice the compression level as the wider band. Continuing with the example above, using bands with less width at the ankle and wider bands proximally would yield graduated compression when the garment is applied to the limb.

Some embodiments of the garment utilize padding or a compressible/semi-compressible liner to affect the sub-bandage pressure. Use of padding under the garment, whether it is cotton cast padding, or foam with various inflection load density (ILD), has a very large affect on the sub-bandage pressure on the skin under the garment. Use of the padding is important to reduce sub-bandage pressure on skin which overlies prominent tendons and bony surfaces (e.g., anterior ankle and the malleoli). These areas may require extra padding to reduce risk of pressure ulceration. Therefore, the garment can be specifically engineered to have the desired subbandage compression results by taking into consideration the padding used, its thickness, and the compression properties of the binder placed over the garment.

In another embodiment, a garment is provided where there is a maximal extension characteristic for the bands in the range of 15-100%. At this maximal extension, the bands are engineered to have a compression level that lies within the range of 8 mm-50 mm. Because of the maximal stretch characteristic, the patient can easily learn to apply the wrap at its maximal stretch. This provides a pre-determined baseline level of compression. Once donned, the garment has additional benefits of augmenting muscle activation to improve venous and lymphatic flow. There has never been such a garment before, and this technology has broad implications for treatment of venous ulcerations, lymphedema, post-operative edema, prevention of re-ulceration, DVT prevention, as well as sports medicine (reduced muscle fatigue, improved recovery with compression).

In one embodiment, a method of assembling short-stretch bands to provide a compression garment is provided considering limb girth and various factors listed above, such as the type of bands selected, to provide the desired therapeutic results. A computer program or algorithm can be written to input the desired compression ratings and the parameters, and then give instructions for how to create the garment that will have the desired compression levels all the way along the affected limb.

In another embodiment, a garment for providing compression force to a limb includes three bands. A first band extends in a direction to wrap around a first portion of the limb; a second band extends in a direction to wrap around a second portion of the limb; and a third band extends in a direction to wrap around a third portion of the limb. Each band includes a first attachment mechanism located at the distal end of the band configured for selectively securing the band when wrapped around the limb. At least one band is configured to provide a different amount of compression from the other bands.

In another embodiment, a garment for providing a compressive force to a limb and a joint attached to the limb includes a liner, a plurality of bands, and a joint compression device. The liner is for use between the limb and one or more of the bands for providing a first compressive force to the limb. The joint compression device is attached to the liner and configured to be positioned adjacent to the joint for providing a second compressive force to the joint.

In another embodiment, a garment for treating an elevated concentration of interstitial fluid in a body area of a patient includes a first plurality of bands. One or more of the bands is connectable to itself to form a closed loop of selectively variable circumference and has a lateral edge portion configured to be interlocked in an overlapping relationship with a facing lateral edge portion of another one of the plurality of bands.

In another embodiment, a garment for providing compressive force to a limb and a joint attached to the limb includes two groups of one or more bands and a joint compression device. The first group of one or more bands provides a first compressive force to a first portion of the limb. The joint compression device provides a second compressive force to the joint. The second group of one or more bands provides a second compressive force to a second portion of the limb. The joint compression device is configured to be positioned between the first and second groups of bands.

In another embodiment, a compression garment includes a plurality of bands of differing compression characteristics. The plurality of bands are configured according to at least one from the group consisting of: the plurality are of different material construction to provide different compression characteristics; the plurality of bands are configured to be arranged with different amounts of overlap with adjacent bands; the plurality of bands are of varying lengths; and the plurality of bands are of varying widths.

In another embodiment, a compression garment includes a plurality of bands. Each band has a maximal extension characteristic in the range of about 15-100%. At the maximal extension, each band has a compression level that lies within the range of about 8 mm-50 mm.

In one embodiment, a method of providing an apparatus for treating an elevated concentration of interstitial fluid in a limb of a patient is provided. The method includes receiving measurements of predetermined components of the limb; selecting a plurality of bands according to the measurements; assembling the selected plurality of bands; and providing the assembled bands to the patient.

In another embodiment, a method of providing an apparatus for a limb is provided. The method includes receiving measurements of predetermined components of the limb and selecting a plurality of bands according to at least one of: limb circumference, limb geometry, maximum stretched length of the band, band width, band un-stretched length, compression level of the band at maximum stretch, and position of the band on a limb portion. The selected plurality of bands is then assembled for use.

In one exemplary aspect, the present disclosure is directed to a sleeve for providing a therapeutic compression force to a limb. The sleeve may include a proximal end and a distal end, with the proximal end having an opening for receiving the limb. The sleeve also may include a first region configured to provide a first level of therapeutic compression greater than 8 mm. It also may include a second region configured to extend along the limb from the first region. The second region may be configured to provide a second level of compression less than the first level of therapeutic compression. In some aspects, the first level of therapeutic compression is greater than 5 mm.

In another exemplary aspect, the present disclosure is directed to a garment for providing compressive force to the limb. The garment may include the sleeve and at least one compression band configured to extend about a portion of the sleeve and configured impart a therapeutic compression to the limb.

In yet another exemplary embodiment, the present disclosure is directed to a garment for providing compressive force to a limb. The garment may include a compression sleeve including a proximal end and a distal end, the proximal end having an opening for receiving the limb. It also may include at least one compression band configured to extend about a portion of the sleeve and configured impart a therapeutic compression to the limb.

In yet another exemplary embodiment, the present disclosure is directed to a garment for providing compressive force to a limb. The garment may include a compression sleeve including a proximal end and a distal end. The proximal end may include an opening for receiving the limb. The sleeve may have a calf area with decreased stretching properties in order to augment venous calf muscle return.

In yet another exemplary embodiment, the present disclosure is directed to a garment for providing compressive force to a limb. The garment may include a sleeve including a proximal end having an opening for receiving the limb. The sleeve may have a first region configured to provide a first level of therapeutic compression and may have a second region configured to extend from the first region and configured to provide a second level of compression less than the first level of therapeutic compression. At least one compression band may be configured to extend about a first portion of the sleeve and configured to impart a therapeutic compression to the limb.

In yet another exemplary embodiment, the present disclosure is directed to a method of treating an elevated concentration of interstitial fluid in a body area of a patient. The method may include determining an appropriate sleeve size and compression rating to cover the body area, the sleeve including: a proximal end and a distal end, the proximal end having an opening for receiving the limb; a first region configured to provide a first level of therapeutic compression greater than or equal to 8 mm; and a second region configured to extend along the limb from the first region, the second region being configured to provide a second level of compression less than the first level of therapeutic compression.

In yet another exemplary embodiment, the present disclosure is directed to a method of treating an elevated concentration of interstitial fluid in a body area of a patient. The method may include determining an appropriate compression sleeve or compression stocking to provide baseline compression to the area and determining an appropriate compression band or bands to use with the compression sleeve to augment reduction of interstitial edema in the patient.

In yet another exemplary embodiment, the present disclosure is directed to a thigh high compression garment for a patient. The garment may include a sleeve having a proximal end and a distal end, the proximal end having an opening for receiving a limb. The sleeve may have a first region configured to provide a first therapeutic compression range of 8-50 mm and may have a second region with a compression range of 0-40 mm. At least two non-elastic or elastic compression bands may be wrappable about the sleeve and configured to apply therapeutic compression to an area distal of the patient's knee. At least one non-elastic, short-stretch, or elastic compression band may be configured to apply therapeutic compression to an area proximal of the patient's knee.

In yet another exemplary embodiment, the present disclosure is directed to a method of treating an elevated concentration of interstitial fluid in a leg of a patient. The method may include placing a first sleeve about a thigh area of the leg of the patient, the first sleeve being configured to impart therapeutic compression to the thigh area. A second sleeve may be placed about a calf area of the leg of the patient, the second sleeve being configured to impart therapeutic compression to the calf area. The method also may include removing the first sleeve from the thigh area of the leg of the patient and maintaining the second sleeve about the calf area of the leg of the patient.

In yet another exemplary embodiment, the present disclosure is directed to a method of treating an elevated concentration of interstitial fluid in a leg of a patient. The method may include placing a first sleeve about a thigh area of the leg of the patient, the first sleeve being configured to impart therapeutic compression to the thigh area. It also may include placing a second sleeve about a calf area of the leg of the patient, the second sleeve being configured to impart therapeutic compression to the calf area. A knee wrap or knee-piece may be placed as a third area about the leg of the patient, the third area being configured to impart therapeutic compression to the knee region.

In yet another exemplary embodiment, the present disclosure is directed to a sleeve for providing compression force to a calf area of a patient's leg. The sleeve may include a proximal end having an opening sized to fit around an upper calf area on the patient's leg, and may include a distal end having an opening sized to fit around a lower calf area on the patient's leg. It also may include a body portion extending between the proximal and distal ends, the body portion being configured to provide therapeutic compression to the calf area.

BRIEF DESCRIPTION OF THE DRAWINGS

FIGS. 1a and 1b are illustrations of different embodiments of a modular compression garment according to the present disclosure.

FIGS. 2a and 2b are perspective views of different embodiments of bands used in the modular compression garment of FIG. 1.

FIG. 3 is a break-away view of the compression garment of FIG. 1 including one embodiment of a spine used for connecting a plurality of bands such as those shown in FIGS. 2a and 2b.

FIG. 6a is a side perspective view of a footpiece for use with a modular compression garment.

FIG. 6b is a block diagram of an embodiment of the compression garment including a plurality of bands and a joint compression member or piece, such as the footpiece of FIG. 6a.

FIG. 7 is a side view of a liner for use with a modular compression garment.

FIG. 8 is an illustration of an order form for ordering a customized compression garment.

FIG. 10b is an inside view of the garment of FIG. 10a.

FIGS. 12a and 12b are illustrations of an exemplary garment according to yet another embodiment of the present invention.

FIGS. 12c and 12d are illustrations of another exemplary garment according to yet another embodiment of the present invention.

DETAILED DESCRIPTION

Figure 4:
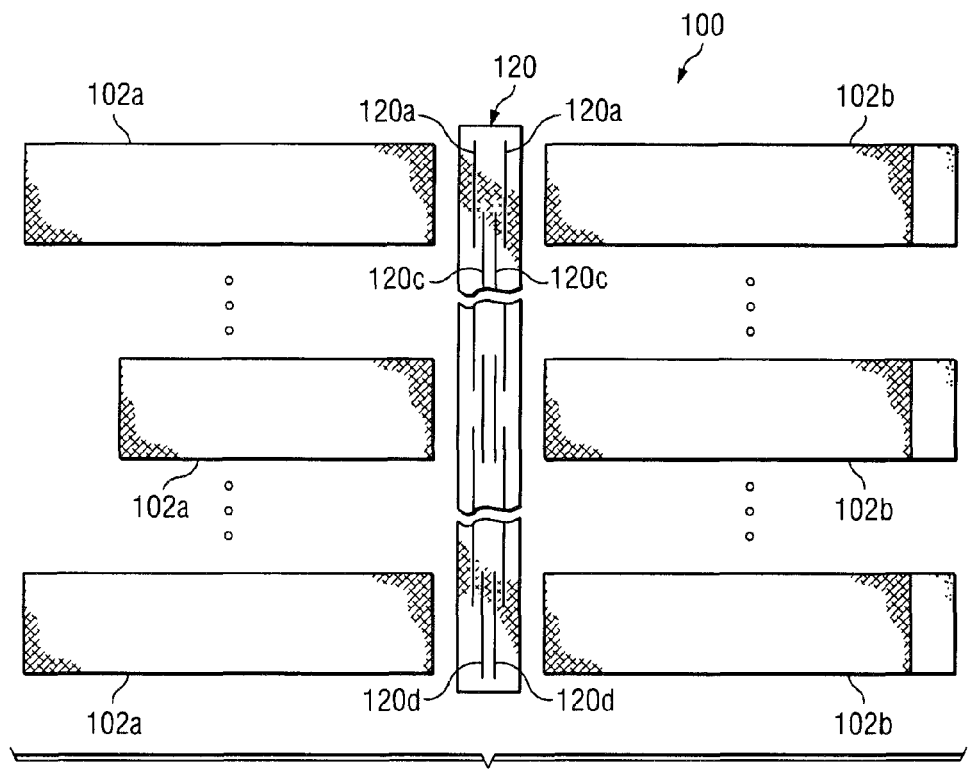
FIGS. 4, 5 and 9 are alternative embodiments of a modular compression garment of the present invention.

The present disclosure relates generally to treatment of edema and, more specifically, to a device for applying compressive pressure to a person's body in order to facilitate reduction of interstitial fluids from a body trunk and/or limb extremity and to provide support and fatigue relief.

It is to be understood that the present disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not, in itself, dictate a relationship between the various embodiments and/or configurations discussed. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact.

FIG. 1a illustrates one embodiment of the present disclosure applied as a lower limb compression garment 100. In this embodiment, the lower limb compression garment 100 includes several bands 102 that are of adjustable size by way of attachment mechanisms 104 for conforming, in the present embodiment, to a human leg 106. The lower limb compression garment 100 also includes an anklet 108 for conforming to a human ankle.

FIG. 1b illustrates another embodiment of the present disclosure applied as an arm compression garment 100c. The garment 100c includes several bands 102 and attachment mechanisms 104, but they may be of different size and have different properties, as compared to one used for a human leg.

It is understood that the present invention is not limited to use with the leg, but can be used in various limbs and trunks of humans. It is further understood the invention is not limited to humans, but may apply for veterinarian use such as for a horse, dog, or other animal. For example, another embodiment may be used to compress an entire leg or arm of a human or a leg of a horse or dog. Various embodiments of the present disclosure may also provide for maximal access to a portion of a limb. These embodiments may have the compression band 102 over the affected area on top, with the proximal and distal compression bands overlapping. This may allow removal of a compression band or bands 102 over the affected area, while not requiring removal of the entire garment. Thus, the rest of the garment 100 may remain therapeutic while the area is accessed.

Referring also to FIG. 2a, in one embodiment, the bands 102 may include an inner layer 114 and an outer layer 112 with optional elastomeric compression material layer 110. In one embodiment an elastomeric loop material 112 such as Shelby Elastics Mon-3 or WonderWrap (Shelby, N.C.) may be sewn onto a backing of elastomeric fabric 114 such as Schoeller® Prestige 58012 (Sevelen, Switzerland). The elastomeric fabric 114 may be sewn on-the-bias so as to provide more stretch. For higher compression for a given amount of stretch, the fabric 114 may be sewn not-on-the-bias. Therefore sewing a highly elastic loop fabric 114 onto the backing of the material 110 or 114 may alternate percentage stretchability and alternate the compression gradient, based upon material selection and if it is sewn on-the-bias or not on-the-bias. Sewing such elastomeric fibers 114 on-the-bias may allow more stretch but less compression. For example, sewing the WonderWrap on the Schoeller fiber on-the-bias may result in a 20-30% elastomeric range with good compression. Sewing the WonderWrap on the Schoeller fiber not on-the-bias may result in a 15-20% elastomeric range with more compression. This way several embodiments can be easily engineered to provide different common classes of compression such as 8-15 mm, 15-20 mm, 20-30 mm, 30-40 mm, or 40+ mm. This may allow the garment 100 to be applied lightly or tighter and more therapeutic. If applied past the range of the therapeutic stretch, then the compression applied may be directly proportional to that the user applies.

Referring to FIG. 2b, in another embodiment, the outer layer 112 may be a thin-napped Lycra material to which a hook-type fastener can readily adhere. One example of such material is produced by Techno-Med Technologies. The inner layer 114 can be made of a compression stocking material for providing enhanced compression. Examples of material for the inner layer 114 include knitted, woven and non-woven elastomeric materials such as weftloc, powernet, techsheen, lockstitch, superlock, triskin, stretch satin, gentilisimo, and tricot. Different models of this material can be chosen for a desired compression effect, and some bands may be made of different materials than others in the same garment 100. The two layers 112, 114 can be joined together using a variety of techniques, including a thin film coating of adhesive by Dartex Coatings (Slatersville, R.I.).

In other embodiments, a thin semi-compressible layer 110 is provided between an inner layer 114 and the outer layer 112 of the bands 102. This layer 110 may be made of polyurethane foam such as Rosidal Soft (Lohmann Rauscher Neuwied, Germany). Such foam would ideally by 0.3 cm thick, although other ranges of thickness 0.05 cm to 5 cm are possible. The layer 110 may include particles made of compressible, high resiliency, low density, open cell plastic foam. Such particles ground up and of different particle sizes and shaped particles can create areas of high pressure areas and intersecting networks of low pressure areas at the seams. Use of such particles for compression garments is known in the art and sold as the Tribute™ (Solaris Inc. Brookfield, Wis.). Other materials for the compressible layer 110 may include rubber, plastic air bubbles, foam air bubbles, or non-convolute foam. The semi-compressible layer 110 may have channels sewn in them to create lines of natural lymph flow or crisscross pattern. Alternatively, in other embodiments the foam may serve as the inner layer with a loop-compatible fabric or elastomeric material as the outer layer.

In still other embodiments, the bands 102 may but consist essentially of elastomeric fabrics such as powernet nylon or nylon/spandex, and ComfortWeave™ polyester/spandex, yarns such as Clearspan® spandex manufactured by Radici, Dorlastan® spandex manufactured by Bayer, Lycra® spandex manufactured by Invista, and/or special woven cotton fabrics such as Comprilan® short-stretch bandage, manufactured by Beiersdorf AG. Another elastomeric compression material that may be used is Lovetex® Industrial Corporation Breathe Freely. It is understood that, in the spirit of the disclosure, any suitable elastic material may be used and is not limited to those listed above. In the present example, the chosen material would be in a range of 15% to 100% elastic stretch, although other ranges are anticipated (including from 5% to 300%).

In still other embodiments, the band 102 may include the elastomeric semi-compressible layer and a thin outer layer of Velcro® (hook and loop) compatible fabric. Such a garment may be sold as a reusable, semi-disposable, or disposable garment. For example, as single-use embodiment might be sold sterile and for application directly after surgery on an affected limb in order to control swelling and prevent wound dehiscence, or to allow selective access postoperatively to access directly over incision or wound, while leaving the rest of garment in tact. Other single-uses may include general hospital use or as outpatient clinic or home use in order to reduce or control interstitial edema. Alternative uses may be to hold a bandage or medication against a limb member.

The attachment mechanisms 104, which are connected to or connectable to the bands 102, allow the bands to interconnect to one another. The attachment mechanisms 104 can be of various types such as hooks, snaps, buttons, and glue/adhesive, and some mechanisms for some bands 102 may be different than those for other bands on the same garment 100. In the example of FIG. 2, the attachment mechanisms include a hook-and-loop fastener, such as a Velcro® strip. Each band 102 may fasten to itself in such a way as the user can apply the band under compression and it will hold the compression against the body part. The hook of the hook-and-loop fastener may be sewn onto one end of the band and the body of the band or a portion thereof may have the loop material.

In this embodiment, some or all of the exterior surfaces 112 of the bands 102 may include elastomeric loop material. The material therefore may interlock with the hook material of the attachment mechanisms 104 and/or a spine (discussed below). The use of loop material along the outside layer 112 of the band 102 allows each band to apply to a wider range of compression. Also, the use of elastomeric loop material may allow the dual function of attachment to the other end of the band, which has hook material, as well providing active compression.

In varying embodiments, the bands 102 interconnect to each other in a temporary, semi-permanent, or permanent manner. The connections may use chemical, thermal, or mechanical bonds. Mechanical temporary and semi-permanent bonds may include hook and loop, snaps, button and button-holes, or ties and eyelets. Mechanically bonded permanent attachments may include methods such as sewing and stapling. Chemical bonding includes methods such as fabric glue and super glue. Such glue is well-known in the art and used extensively in the industry for upholstery, furniture, and other products. Other forms of chemical bonding include tape adhesive such as PEELnSTICK and the acid-free acrylic double-sided adhesive SuperTape (Therm O Web, Wheeling Ill.). Thermal bonding may include iron-on interfacing, ultrasonic welding of compatible components, or thermal melting of compatible components or iron-on interfacing. Such iron-on interfacing may for example include one or more layers of HEATnBOND® Ultrahold (Them O Web, Wheeling Ill.). Some of the bonds (e.g., hook and loop) allow the garment 100 to be reused many times. Other bonds (e.g., fabric glue) may allow the garment 100 to be reused only a certain number of times. For example, the fabric glue may be reusable for a period of days, but afterwards may loose its adhesion properties. Still other bonds (e.g., thermal welding) are for a single use.

For example, a lower perimeter 114a (towards the foot in the present embodiment) of the interior layer 114 may include a relatively soft hook material. The soft hook material 114a may overlap on the band 102 immediately below, thus interlocking between the adjacent bands and providing additional stability of the device. Alternatively, an upper perimeter 112a (away from the foot in the present embodiment) of the outer layer 112 may include hook material. The lowest band may attach to loop material sewn onto the anklet 108 or attach to the elastomeric loop band at the top of the footpiece. In some embodiments, there will be no soft hook material at the facing edges of the bands and the bands will simply overlap each other with the lowest band overlapping an anklet or footpiece.

Small geographic symbols may be drawn or printed on each band 102 which will change shape in a characteristic way when the proper compression is applied so that the user knows the prescribed therapeutic compression is being applied. Such symbols are well known in the art, and are applied currently to short-stretch bandages such as sold by SSL International PLC under the trade name of Setopress (London, England). In another embodiment, material color or material markings will differentiate different bands of varying levels of compression.

Figure 5:
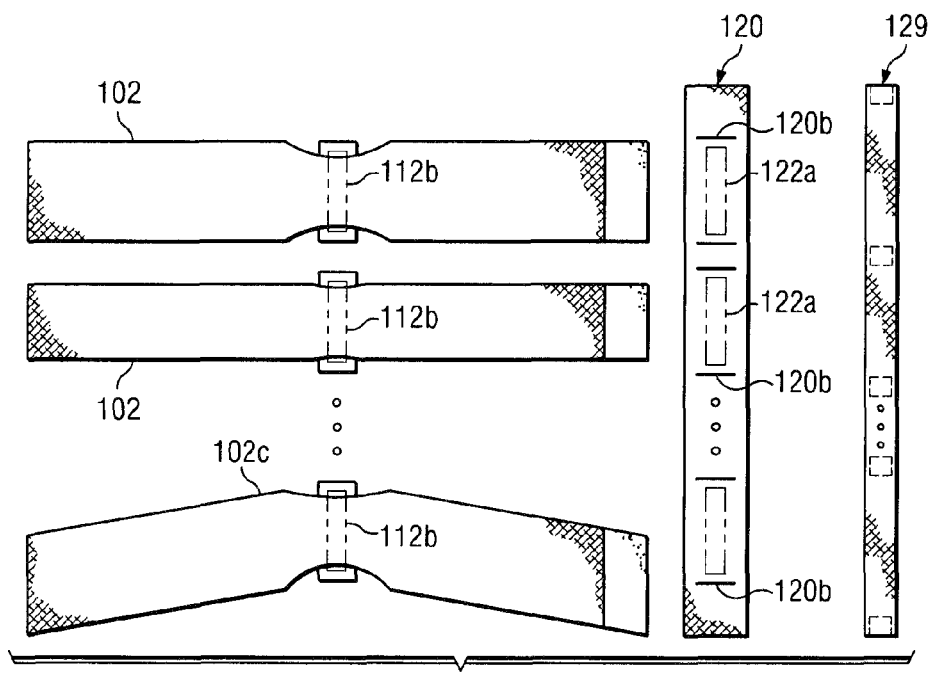

The bands 102 can be in various configurations with each other. For example, in FIG. 3, the bands 102 are shown to be in an overlapping configuration. In FIG. 4, the bands 102 can either be spaced or overlapping, depending on which slit 120a, b, and/or c is being used. In FIG. 5, the bands 102 are touching but not overlapping each other, while a band 102c is spaced from an adjacent band 102 immediately above.

Referring now to FIG. 3, in one embodiment, the bands 102 are joined together at a spine 120. The bands 102 can be joined to the spine 120 in various manners, and in the present embodiment they are sewn together. The spine 120 may comprise non-elastic or elastic material. There may be no difference in bulk or therapeutic application of this embodiment. Furthermore, the bands 102 may be partially or completely sewn together. In this embodiment, the bands 102 and spine 120 may be separately pre-manufactured, and then sewn together once measurements are made of the affected limb. By modifying the degree of overlap of the bands and the number of bands, a wide geometry of limbs may be fitted. The anklet 108 (FIG. 1) may be sewn to either or both of the spine 120 and the adjacent band 102.

In the embodiment of FIG. 3, the spine 120 extends both on an inside (adjacent the leg) and outside (external) of the lower limb compression garment 100. In furtherance of the example, the spine 120 includes hook material 122 for engaging with loop material 124 on the bands 102 (the loop material can be on both the inside and outside portions of the bands). An outer layer 126 is also provided, which may be either relatively stiff or rigid, which can facilitate the assembly and fitting of the lower limb compression garment 100, or may have elasticity which can facilitate the movement of the lower limb compression garment once in place.

Other embodiments may use one spine, one on the inside or one on the outside. Other embodiments may forego the spine. In some embodiments without the spine, the fastener, other connective means, and/or overlapping may provide adequate connection to hold the device together as a single unit for application or storage.

In some embodiments, the spine 120 may also serve to connect the anklet 108 (FIG. 1). In other embodiments, the bands 102, spine 120, and/or anklet 108 can be attached using other mechanisms, such as glue or adhesive, snaps, or buttons. Furthermore, the spine 120 can be sewn or otherwise segregated into increments 128 so that it can easily be cut or shortened, as needed. For a lower limb, the spine may be 12, 13, 14, or 15 inches in length with increments, although single lengths of spine for different uses are within the scope of the present disclosure. For use as an upper limb compression device, for example, the spine may preferentially go the entire length of the arm along the outside edge. This may necessitate a longer spine and such permeations are within the scope of the present disclosure. Additionally, the spine may wrap around from one side to the other to allow for attachment of excess length or for additional stability of the device. Additionally, it is understood that other modular configurations exist within the scope of the present disclosure, such as any other attachment of the spine to the compression bands or method of attachment of one band to another. These may include buttons, snaps, zippers, or other methods of attachment.

Referring now to FIG. 4, in another embodiment, there are two bands, designated 102a, 102b, for each band "level." These bands 102a, 102b interconnect to each other and/or the spine 120. The spine may include slits 120a, 120c, 120d to assist in interconnection of the garment 100. The interconnectivity of the spine 120 to the bands 102a, 102b may be any method of mechanical, chemical, or thermal. In the present embodiment, the slits for each band 102a/b alternate on either side of the spine 120 so that the bands can overlap. For example, the slits 120a are on one side of the spine 120 and adjacent slits 120c are on the opposite side, with a portion of each slit overlapping. In this example, the slits 120a, 120c, 120d do not extend all the way through the spine 120. In another embodiment, the slits 120a and 120c (and so forth) may not lie on the same line. For example, the slits 120a can be offset to one side of the spine, while the slits 120c can be offset to the opposite side of the spine. In another example, the slits 120*a* are further separated from each other than the slits 120*c*. In this way, the slits 120*a*, 120*c* allow the bands 102 to overlap.

In another embodiment, a single band (102, FIG. 1) can be fed through the slits 120*a* to position each band on the spine 120.

Referring to FIG. 5, in yet another embodiment, the spine 120 includes horizontal slits 120*b* and an optional cover member 129. The bands 102 fit against the spine 120 and may or may not attach at positions 122*a* for the spine and 112*b* for the band. The cover member 129 can then be woven in and out of the slits 120*b* in order to hold the bands against the spine. Also, the bands 102 can include projections to interact with the slits 120*b*. The cover member 129 may attach just at the ends, or may attach at locations between each band 102. Again, any interconnections may be temporary or permanent and may include mechanical, chemical, or thermal bonds or a combination thereof.

Figure 9:
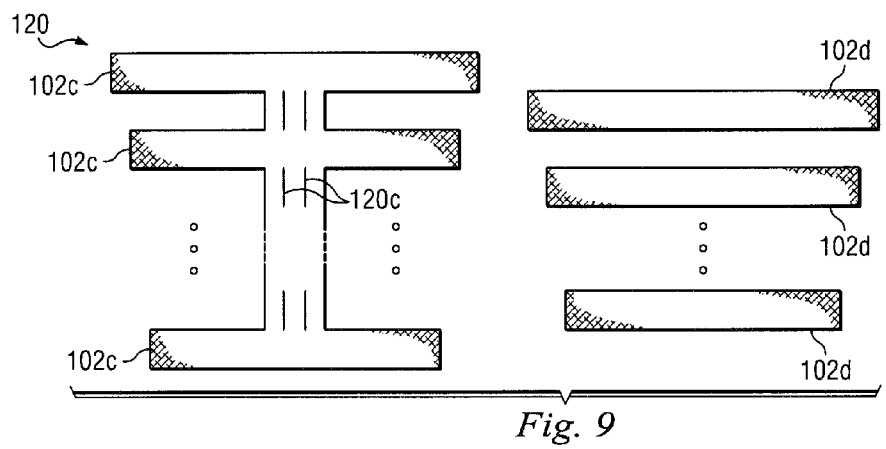

Referring to FIG. 9, in still another embodiment, the spine 120 is formed together with (e.g., formed from the same sheet of material) as some of the bands 102, identified as bands 102*c*. The spine 120 may include additional material to give the spine properties that are different from the bands 102. The spine 120 in one embodiment includes vertical slits 120*a* for receiving another group of bands 102, identified as bands 102*d*. The bands 102*c* fit in the vertical slits 120*a*. As before, any interconnections may be temporary or permanent and may include mechanical, chemical, or thermal bonds or a combination thereof. In another embodiment, there are no slits in the spine and the other group of bands 102 attach to the spine 120 by other attachment mechanisms as discussed above.

Not all of the bands 102 need to be similarly constructed. For example, one of the bands in FIG. 5, designated with reference numeral 102*c*, is formed as a chevron, connecting with the spine 120 at the apex of the chevron. Such shape of a band may be desirable to create a more ergonomic angle on the limb. Such angles are preferably applied perpendicular to the skin, with more angle around the upper and lower curves of the calf than the rest of the garment. Such angles may vary according to limb geometry and garment size. Also, different bands can have different levels of elasticity. This would allow the garment 100 to be placed in different scenarios, such as over a bladder used for pneumatic pumps for preventing deep veinous thrombosis. Also different levels of compression can be provided for bands 102 nearer the ankle (or wrist, or shoulder) than further away from the ankle. This selection of a specific elasticity can therapeutically treat edema or decreasing vein size to prevent blood clots by providing gradient compression to the affected limb.

Furthermore, bands 102 can have different amounts of compressions and expansion, either compared to each other or different amounts along the band itself. Using different levels of compression may be desirable for different garments. Further, graduated compression may be accomplished by using bands of various levels of compression in the same garment. For example, generally more compression may be desired in the ankle portion and less proximally for a leg compression garment. By using different band composition to vary the stretch, different levels of compression may be achieved. In another example, a band may have less stretch in the portions that intersect the spine 120, and more compression near the ends that are used for the locking mechanism 104. Thus, an assembled device can therapeutically apply varying levels of compression. When the user feels that the band no longer stretches, then the compression becomes different and proportional to the tension placed on the band. The user can thus learn to "dial in" to this difference and so more reliably and predictably apply the desired level of compression. By varying the length and width of a band and/or the composition of the band, any desired level of compression can be created in the band.

Referring again to FIG. 1, in another embodiment, the anklet 108 can be configured as an ankle high, knee-high or thigh-high sock or stocking, being relatively thin so that a shoe can be worn over the garment. In one embodiment, the anklet 108 is made of a synthetic stretch-fiber fabric such as a Lycra® brand spandex-containing material in a knitted, woven or non-woven construction. In some embodiments the anklet 108 may or may not fasten to the rest of the garment 100. For example, a compression anklet or stocking can be used and placed in position with, but not attached to, the garment 100. In FIG. 1*b*, the tubing material may or may not provide additional therapeutic compression. The material may furthermore be attached to the spine or may itself form the spine of the garment.

Referring now to FIG. 6*a*, in another embodiment, a footpiece 130 can be used as a different kind of anklet. In one embodiment, the footpiece 130 includes an inner sock-like member 132 of cotton/Lycra blend and three outer bands 134*a*, 134*b*, 134*c* of elastomeric material. Other materials and construction can be chosen in order to alter the compression level of the device. Construction may be made of same materials and layers as in FIG. 2. In some embodiments, the material may be an elastic or non-elastic material and of one single layer or many overlapping layers.

The three elastomeric bands 134*a*, 134*b*, 134*c* are arranged so that the first elastomeric band 134*a* fastens over the forefoot, the second elastomeric band 134*b* is angled at approximately ninety degrees to the surface of the midfoot, and the third elastomeric band 134*c* is fastened parallel to the back of the Achilles. In the present embodiment, the third elastomeric band 134*c* is unique from the other two in that it can attach in place across, or across and downward onto the dorsum of the footpiece. Thus the design is unique in that it allows to fit a variety of foot sizes and to apply variable compression as desired to be most therapeutic.

The footpiece 130 also includes a single band 134*c* sewn in place in the middle with both free ends with sewn hook material. The hook material may be fastened circumferentially across just below the ankle, or may reach down toward the forefoot and across to the opposite side, for example. The flexibility of this band allows a number of geometries to be accounted for. In one embodiment, the band is just over three inches wide. The length of the band may be any desired length for therapeutic use. For example, lengths of 6 inches, 8 inches, 10 inches, 12 inches, 14 inches, 16 inches, and 18 inches, or other lengths are possible.

Referring now to FIG. 6*b*, as discussed above, the garment 100 can include a plurality of bands 102 and a joint compression member or joint piece, such as an anklet or footpiece. In another embodiment, the garment 100 can include a plurality of bands 102 and knee piece or knee wrap. In yet another embodiment, the garment 100 can include a plurality of bands 102 and elbow piece or elbow wrap. In still another embodiment, the garment 100 can include a plurality of bands 102 and a wrist wrap.

Referring to FIGS. 1 and 6, a stocking liner 140 may be provided under the garment 100 to reduce itching and minimize effects of overlapping on the skin. The liner can extend the entire length of the garment 100, including any ankle 108 or foot piece 130, or may cover only a portion thereof. The liner 140 can be formed of a cotton/Lycra® blend or other material and may have a foam lining. The foam lining may include sewn channels to follow the body's natural lymphatic drainage lines. The foam lining also may have foam with stitches or carved portions to create a waffle-like pattern in order to facilitate lymphatic drainage in the un-compressed portions. The thickness of such a liner 140 may be quite thick, such as can be achieved with the JoviPak UE-P-AG1 (Tri-D Corporation Kent, Wash.). The foam may include a granular-type material. A fabric cover may also be included on all or part of the foam lining.

Referring also to FIG. 7, the liner 140, shown here being used with an arm compression garment, would have a multiplicity of pressure-applying resilient protrusions, or high pressure areas 142 and channels 144 there between. The channels 144 potentially facilitate lymphatic drainage while reducing interstitial edema along the high pressure areas 142. The liner 140, which may be constructed similarly to commercial products known under the brand JoviPak, Tribute™ or Komprex II, may be a cotton or blended material with thicker woven fabric as seen in many commercially available socks.

In some embodiments, the channels 144 of the liner 140 can be sufficiently rigid to further allow any bands 102 (see e.g., FIG. 5) to be spaced apart from each other and still provide sufficient compression.

Another embodiment of the liner 140 may include one or two layers of cotton or cotton/Lycra blend or another similar woven or formed material, with semi compressible material woven between the inner and out layers of the liner. The liner 140 may also include the channels 144 which are in the form of sewn pockets with openings 146 for insertion of a semi-compressible insert 148 to form the high pressure areas 142. Such an embodiment may have distinct advantages over other commercially available liners since it may be much thinner but with similar performance. This allows more comfort for long-term wear and improved breathability of the liner 140. The liner 140 may be designed for a specific use, but may have additional uses under other commercially available compression devices, such as The Cinch (Innovative Medical Solutions, Seattle Wash.), ReidSleeve (Peninsula Medical Inc., Scotts Valley Calif.), short-stretch or medium-stretch bandages, CircAid (San Diego Calif.) or other commercially used products for treatment of edema, venous and lymphedema. The insert 148 is preferentially thin and less than 1 cm, although larger sizes may also be desirable.

In another embodiment, foam padding can be positioned in-between the liner 140 and the straps 102. The foam padding can be used to reduce lymphedema. One possibility is to use dense foam such as Komprex foam (Lohmann Rauscher Neuwied, Germany). In this embodiment, the foam is cut into small squares of 0.25 cm to 2 cm along each side. These squares may or may not have a pyramid shape facing the inner layer. These pyramid-shaped areas massage the affected area during wear and can break up fibrotic areas, effectively reducing lymphedema long-term. Alternatively, one solid piece of foam with a grid but out on one side may achieve the same function. Other foam padding includes JoviPak Multi-Purpose pads (Tri-D Corporation Kent, Wash.) or other commercially available products such as the Jovi Le-C-Advi sheet foam liner. Such pads are sewn chips or pieces of polyurethane or similar foam and may or may not have channels sewn into place.

Figure 10A:
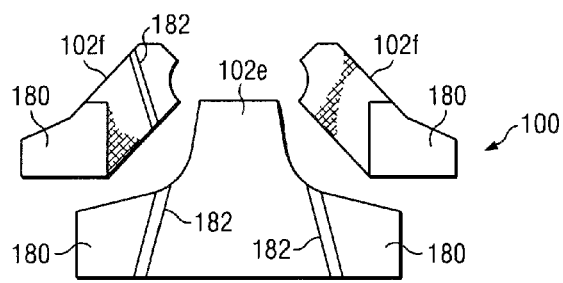
FIGS. 10a and 10c are outside views of a garment according to anther embodiment of the present invention.
Figure 10B:
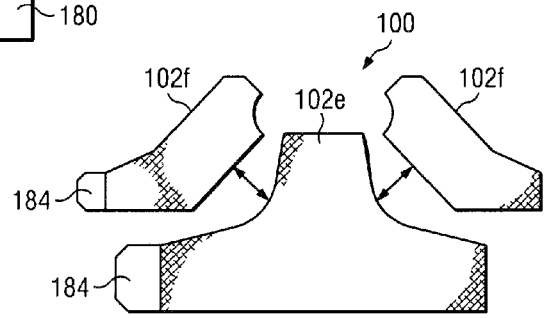
Figure 10C:
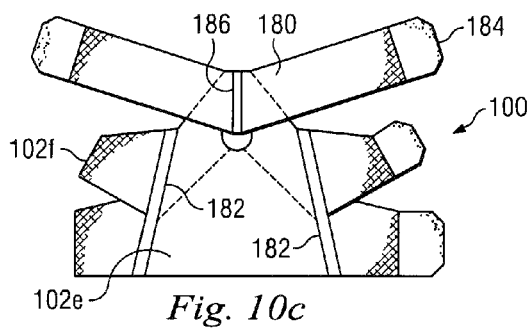

Referring to FIGS. 10*a*, 10*b*, and 10*c*, in another embodiment, the garment 100 can be assembled with a spine that is built-in to the bands. A first band 102*e* includes a portion of webbing material 180 sewn thereon, as well as two strips of loop material 182 and a portion of hook material 184. A next group of bands 102*f* also include the sewn-on webbing material 180 and the loop material 182 and hook material 184. The bands 102*e*, 102*f* can be configured as shown in FIG. 10*b*.

Additional bands 102*g* can then be added, as shown in FIG. 10*c*, with additional webbing material 180 sewn on as well as loop material 182 and hook material 184. As a result, the garment 100 can be assembled piece-wise, as shown.

In some instances, the garment can be assembled using a material glue or cement that secures the webbing materials to each other. Accordingly, assembly of the garment from the modular components may be simplified and efficient. Using such methods, as well as the other methods disclosed herein, may permit custom garment orders to be filled while the patient waits.

Figures 11A, 11B:
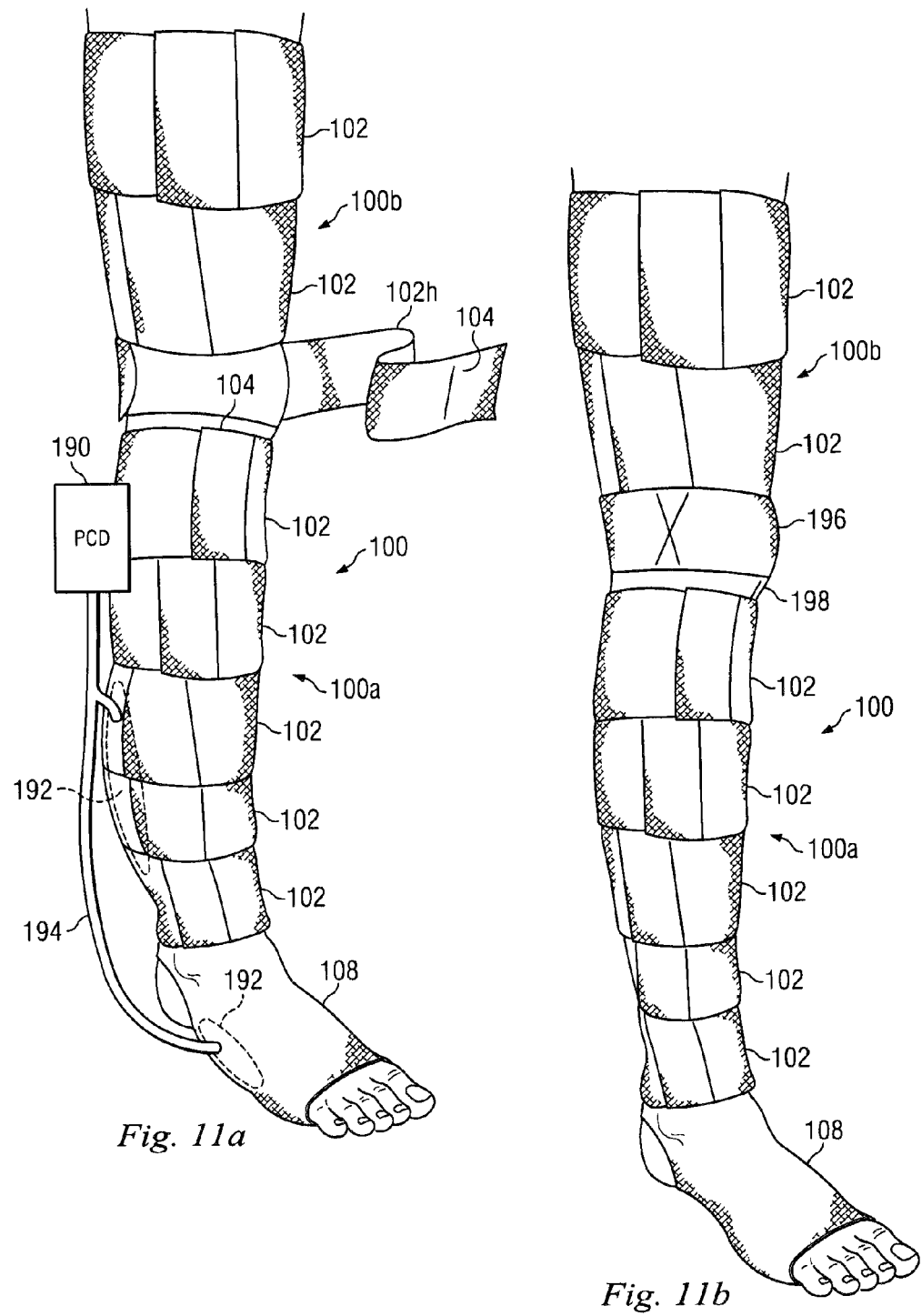
FIGS. 11a and 11b are illustrations of a pair of garments according to yet another embodiment of the present invention.

Referring to FIG. 11*a*, in another embodiment, two different garments, designated 100*a* and 100*b*, can be used. In the present example, the garment 100*a* is similar to the garment 100 of FIG. 1*a*, and is placed around the lower leg. The garment 100*b* is placed around the thigh. Such an arrangement can be very beneficial for reducing blood clots, such as during a knee surgery operation. The garments can be of different construction. For example, the lower garment 100*a* can be of a longer-lasting, less-elastic, reusable material, and the upper garment 100*b* can be made of a more-disposable, more elastic material.

In the illustration of FIG. 11*a*, the knee is exposed, and can therefore be examined and/or operated on with one or both of the garments 100*a*, 100*b* in place. In the alternative, a band 102*h* can be provided to further wrap the knee. In the present example, the band 102*h* is very long, and can wrap the knee multiple times before being secured with the fastener 104. Fastener 104 may be attached to garment 102*b*, be separately applied, or be interconnectable to garments 102*a* and/or 102*b*.

Referring still to FIG. 11*a*, in some embodiments (including all the embodiments discussed above), a pneumatic compression device (PCD) 190 can be incorporated with the garment. In the present example, it is incorporated with the lower garment 100*a*. One example of a PCD is a DVT pump. The PCD 190 connects to one or more air bladders 192 through tubing 194. The air bladders 192 can be sewn into one or more bands 102, or a pouch may be provided in the garment 100*a* to receive them.

Referring now to FIG. 11*b*, in another embodiment, the two garments 100*a*, 100*b* can be interconnected by a knee piece 196. The knee piece 196 may be constructed of a knitted, woven, or non-woven elastomeric fabric, including those listed above. In the present embodiment, the knee piece 196 is a slip-on sleeve that can stretch in multiple directions. Also in the present embodiment, the knee piece 196 is sewn into the lower band 102 of the upper garment 100*b*, but attached to the lower garment 100*a* through an optional hook fastener 198. It is understood that other fastener systems can also be used.

Referring again to FIG. 1*b*, in this embodiment, the garment 100*c* includes a stocking 140. The stocking 140 can be similar to any of the stockings discussed above. In the present embodiment, the stocking 140 includes a portion that functions as the spine 120. For example, the stocking can be made in whole or in part of a material that can attach to the bands 102 through various attachment mechanisms. In furtherance of this example, the stocking can include an outer surface that connects to a hook-type material (of a hook-and-loop fastener system) on the bands 102. In another example, the stocking 140 includes several slits, as discussed above, which can engage with the bands. In yet another example, the stocking 140 includes a strip of different material, or of different physical property to provide the spine 120. In furtherance of this example, a strip of more-rigid or hardened material can be provided to serve as the spine 120 and can thereby receive the attachment mechanisms for receiving the bands 102.

The stocking 140 may further be attached or included with the anklet 108. The anklet 108 can be of any type discussed above, including cotton, Lycra, elastomeric material, or combinations thereof.

Referring now to FIG. 8, the garments 100 discussed above can be provided in response to receiving a customer order form 200. The form 200 includes an order information section 202, a shipping information section 204, a billing information section 206, a measurement section 208, and a measurement guide 210. A customer can obtain and fill out the form 200 where measurements are taken of key components of the affected limb. If the place of assembly for the garment 100 is the same as the place of sale, then the measurements may be compared to pre-stocked components and the proper number and type of components can be selected. The modularity of the garment 100 facilitates a sales facility in having a reduced inventory yet still being able to provide a highly-customized solution.

Furthermore, the amount of overlap of bands may be varied to accommodate a variety of leg lengths. In one embodiment, the bands 102 are just over three inches in height, and each lower limb compression device may have 4-6 bands, one to two spines 120, and a footpiece or anklet 108. Since the spine 120 may be modular, one spine may accommodate an arm or a lower leg. Other spines, such as for an entire lower limb device, may also be provided. In another embodiment, the spine 120 may include a material backing with iron-on interfacing. This will allow quick permanent assembly of a plurality of bands 102 with or without an anklet. This customization can be done at the time of measurement of the actual limb, or can be done at a remote location using the measurement form 200.

In some embodiments, one or more of the bands 102 can be overlapped and connected (e.g. sewn together) prior to delivering to a doctor or patient. In other embodiments, some or all of the garment 100 can be sterilized prior to delivery.

Some embodiments of the form 200 can include information that would allow a doctor or provider to custom select certain bands 102 for different purposes. For example, different levels of edema (e.g., minimal, extreme) can be addressed by selecting an appropriate elasticity of the bands 102. Also, the height and/or weight of a patient can factor into the selection of band size, placement (e.g., more elastic bands near the ankle) and composition. The bands 102 can include a marker such as a position number that will indicate their placement on the spine 120.

Even the girth of the limb is an important factor. LaPlace's law states that the girth of the limb is inversely proportional to the sub-bandage pressure on the limb. Thus, the same band applied with the same tension to a small limb will have higher pressure than a similar band applied with the same band to a tighter limb. Therefore, for patients with very small limbs such as pediatric patients, the present method provides an arrangement of bands with comparatively less compression.

Some applications for use of the invention may be at the recommendation of a treating medical professional. In some examples, a treating medical professional receives a patient and diagnoses a condition of edema. After diagnosis, the medical professional may determine to treat the condition using a compression garment, such as the compression garments disclosed herein. To do so, the medical professional determines a proper size of garment for the patient. The proper size may be based on, for example, patient body measurements, the level of edema, and/or other factors, including those described above. The medical professional may prescribe the garment to the patient. The prescribed garment may be any of the garments or portions of the garments disclosed herein. As used herein, the term medical professional is intended to include a treating nurse, physician, or other individual, as well as any assistants acting on behalf of the treating nurse, physician, or other individual.

In some exemplary situations, the order form may be filled out by a person without training in a medical field. For example, the garments disclosed herein may be available as over-the-counter items. Customers may purchase the garments in person, by mail, over a telephone, or over the internet, for example. When purchasing over the internet, the wholesale or retailer may make information available on the internet that allows a customer to enter measurements and may include an on-line calculating system to determine the size of garment required to treat the edema, and may recommend customized manufacturing of the garment to provide proper therapeutic compression. In one example, an order may be received from a customer for a custom therapeutic compression garment by displaying to the customer a plurality of selectable links that each indicate a different limb of the body. For example, the selectable links may include a thigh, a leg, a foot, and an arm. Once the link is selected a diagram may be provided to the customer with locations on the limb identified for requested measurements. These measurements may be entered in text boxes. A sale price may be calculated based on at least two of the input measurements and the sale price may be displayed to the customer. For example, if the customer were to purchase a custom made therapeutic compression garment for a leg, he or she may select a leg link, and be provided with a diagram of the leg. The diagram may identify requested measurement locations such as, for example, at the widest calf circumference, at the base of calf circumference, at the least ankle circumference, and a height measured by following a contour of the leg, among others. The customer may input these measurements so that they are received into the system. From these measurements, a price may be calculated and displayed to the customer.

In some exemplary situations, a medical professional or a lay person may be provided with a kit including information for determining a suitable garment to reduce edema. The kit may contain, for example, instructions for taking measurement of the limb to be treated, including, for example, length, circumference, among others. It also may include a form, such as the form 200 in FIG. 8, for recording any measurements. Some kits may include information for determining a desired therapeutic compression to treat a condition. Some kits also may include a measuring device, such as a measuring tape.

In some instances, a kit may be requested by, for example, e-mail, over the Internet, through a regular mail, by facsimile, or over the telephone. The kit may be delivered to the customer using a standard carrier or other delivery method. In some examples, the kit may be sent by e-mail or may be accessed over the Internet and printed using the customer's computer.

Following the instructions in the kit, the customer may record measurements on the form for the person to be treated. This may be accomplished manually or electronically by directly entering values into a form accessed over the Internet or other network. The form then may be delivered to a garment supplier. Delivery may occur over the internet, by e-mail, fax, mail, or over the telephone, or using any other delivery method. The supplier then would provide the garment based on the measurements taken.

The garment provided may be any of those described above, but also may include a hybrid garment or an independent sleeve for treating excessive interstitial fluid accumulation, or edema.

FIGS. 12-23 disclose hybrid garments and sleeves that may treat edema. These include features that differentiate them from known compression stockings for treating edema. Known compression stockings are low profile and so work with a wide range of shoes and clothing items, and can be fairly non-conspicuous even with dress shoes. However, these known stockings can be difficult to don and doff, and may require donning devices to make this process less difficult.

However, a completely new hybrid type of compression garment may assist in reducing these difficulties. For example, the new hybrid type of compression garment may include features of a compression stocking and also may include features of a compression wrap with elastomeric or non-elastic properties. This hybrid garment may provide superior augmentation of lymphangion and venous calf muscle function than a comparable traditional stocking and may be easier to don and doff.

FIGS. 12a-12d show embodiments where the limb portion of a garment, referenced in the figures by the numeral 300, includes a compression stocking or is a microfiber sewn elastomeric fabric sleeve 301 sewn to fit the limb. This garment 300 may provide compression to the limb in the range of 8-50 mm, and in some embodiments, may have graduated compression with higher compression distally than proximally. In addition, the garment 300 may include at least one band 102 of short-stretch or non-elastic material which in the embodiment shown is centrally located over the calf muscle area of a patient's leg. This band 102 may be either separate from the sleeve 301, sewn to the sleeve 301, or selectively attachable to the sleeve 301 by hook and loop fasteners, snaps, or buttons, among other fasteners. FIGS. 12a and 12b show one exemplary embodiment, with a single band 102 which covers the calf area. FIGS. 12c and 12d show another exemplary embodiment, including two bands 102 which cover the calf area with one of the bands 102 covering the upper calf area and one of the bands 102 covering the lower calf area.

In one embodiment, there is at least one compression band which is designed to fit over the calf area of the limb. The garment may contain multiple bands which may overlap. These bands are designed to be elastic, non-elastic, or short-stretch elastic. In one preferred embodiment, the bands have 15-100% maximum stretch and compression range of 8-40 mm at maximal stretch. This embodiment is quite important as it represents a completely new approach to compression therapy. In this case, the patient may wear a knee high or thigh-high compression stocking (8-15 mm, 15-20 mm, 20-30 mm, 30-40 mm, or 40-50 mm), and find that the stocking improves edema control but does not completely control it. The user then can don this small wrap, designed to work over the calf area, to further augment venous return. If the patient is active in moving the calf muscle, they will find that even a small non-elastic, short-stretch elastic, or elastic compression over the calf area will control their edema much better than the stocking alone. This embodiment would additionally be very inexpensive to mass-produce, would encourage patient to exercise the calf muscle while wearing the garment, and may very well provide a significant improvement to compression therapy as is known in the art. In some embodiments the band(s) will be sold separately, and in some embodiments they may be sold with a traditional compression stocking. In another embodiment, the band(s) may be selectively detachable or permanently attached to the stocking. The garment may further be a single use or limited reusable type garment.

Other embodiments may include even more than two bands 102. In some embodiments, these bands 102 together may cover the patient's leg from the ankle area to the upper calf. In some embodiments, each band 102 extends circumferentially around the limb and interconnects with itself, for example, by hook and loop fasteners, snaps, buttons, hooks, or other fasteners. As explained above, the bands 102 may include fasteners or attachment mechanisms 104 operable to secure the band about the limb to provide a therapeutic compressive force. The attachment mechanisms 104 may be any of the mechanisms described above, and may include, for example, hooks, snaps, buttons, and glue/adhesive, among others. Some mechanisms for some bands 102 may be different than those for other bands on the same garment 100. In some embodiments, some or all of the exterior surfaces of the bands 102 may include elastomeric loop material, while the attachment mechanisms 104 may include hook material. The loop material therefore may interlock with the hook material of the attachment mechanisms 104. These bands 102 may be important in that they can be applied at maximal stretch to augment calf muscle function of venous return and to augment lymphangion function to improve lymphatic outflow from the limb.

It is important to note that embodiments of this garment that have short-stretch only over the calf muscle area, may reduce edema in the entire limb. The garment would thus help prevent venous ulceration in the ankle, even though the garment is applied proximally over the calf area. Similarly, the garment could be designed to be applied over any muscular area of a limb to augment venous and lymphatic flow to the entire limb area, including areas more proximal and distal to where the garment is actually applied.

By using one or more bands, such as a short-stretch or non-elastic band to improve calf muscle venous return, the garment 300 may outperform known compression stockings that have higher compression. Because the present invention has a solution with less compression than known compression stockings, it may be easier to don and doff. Thus, such a garment would have innovative and desirable place in the marketplace to improve edema control and related complications.

Although the garment 300, with the sleeve 301 and bands 102 are shown treating a lower leg of a patient, it is understood that this invention may be used to treat excessive interstitial fluid accumulation in other parts of the body. For example, one embodiment of the garment 300 is configured to treat a thigh. Some embodiments may include a sleeve extending from the foot to the thigh, while other embodiments may include a sleeve extending from an area above the foot to the thigh, such as, for example, from the ankle to the thigh. Other embodiments include a sleeve and band for treating an arm. It is further understood that these bands can be applied over any area where additional therapeutic compression is needed to control interstitial edema formation.

Furthermore, the garments disclosed herein are not limited to treatment of interstitial edema in humans, but can have application for animals too. For example, some garments may be formed to fit limbs of animals, such as a dog, a horse, or other animal.

Figure 13:
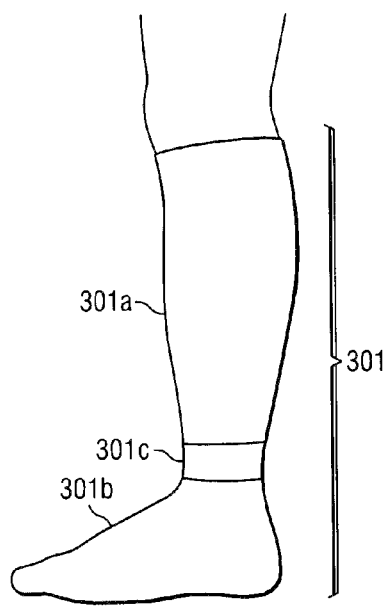
FIG. 13 is an illustration of an exemplary sleeve that may be included as a part of a garment according to yet another embodiment of the present invention.
Figure 15B:
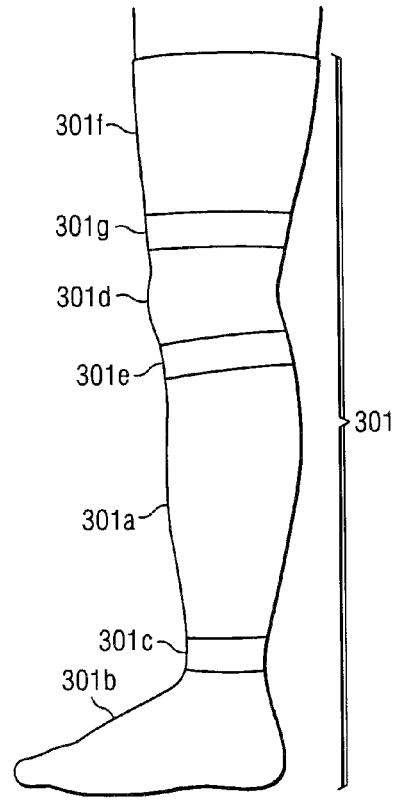
FIG. 15b is an illustration of an exemplary sleeve usable on a leg of a patient according to an embodiment of the present invention.

In another embodiment, the garment includes a hybrid sleeve or liner that has at least two areas of, for example, very different compression. FIG. 13 shows an exemplary embodiment of such a sleeve, referenced by the numeral 301. The sleeve 301 may be used as a part of the garment 300 as shown in FIGS. 12a-d, or alternatively, may be used without the bands 102 on its own, as shown in FIG. 13a. In FIG. 15b, the sleeve 301 includes a high compression region 301b distal to the ankle region and a proximal region of much lower relative compression 301a. The sleeve 301 may include an optional transition zone 301c between the two high and lower compression regions 301a, 301b. The transition zone 301c may provide a third region of graduated transition between the low and high compression regions 301a, 301b. In the exemplary embodiment shown, the transition zone is configured to be disposed adjacent to and proximal of the ankle area. Furthermore, it is contemplated that the distal portion of the sleeve 301 may include portions of less compression, such as less compression to the toes and heel. The high compression region 301b may provide a therapeutic compression in the range of, for example, 8-50 mm compression. In other embodiments, the compression is 15-20 mm compression, while in others, the compression is 20-30 mm compression. The lower compression region 301a may provide therapeutic or non-therapeutic compression in the range of, for example, 0-40 mm.

As explained above, the sleeve 301 may be used as a part of the garment 300 and may be associated with a system of one or more bands 102, such as at least two bands 102, which may be short-stretch elastic or non-elastic. These bands may overlap each other, exactly meet, or have a space between them. In some exemplary embodiments, these bands 102 are located proximal to the high compression region 301b of the sleeve 301. It is understood that the most distal band(s) may overlap the high compression region 301b and/or the transition compression region 301c, thereby providing higher compression at those regions.

In some embodiments the lower compression region 301a of the sleeve 301 is formed of a compression material sewn into a tube forming a first layer. A foot portion forming the high compression region 301b, formed in one example of a knitted material, may be attached to a distal end of the tube as a second layer, with the tube and the foot portion together forming the sleeve 301. In this embodiment, the tube portion may be formed by wrapping material and connecting ends along a longitudinal seam. A flat-knit type of stitch can be used to create a low profile seam for such a garment. Alternatively, the tube may be seamless. Multiple portions also could be used to create the tube, creating multiple seams. Other embodiments also are contemplated such as a compression sleeve with anklet or detachable second sleeve to cover the ankle area.

Figure 14C:
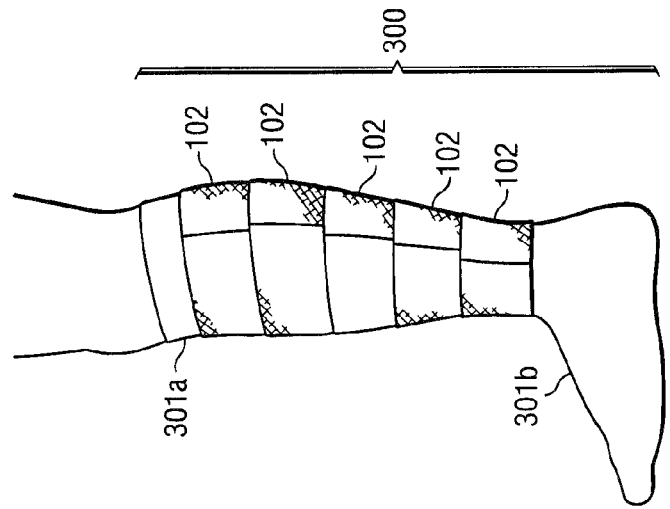
FIGS. 14a, 14b, and 14c are illustrations of an exemplary sleeve and exemplary bands that may cooperate to form a garment according to yet another embodiment of the present invention.
Figure 14B:
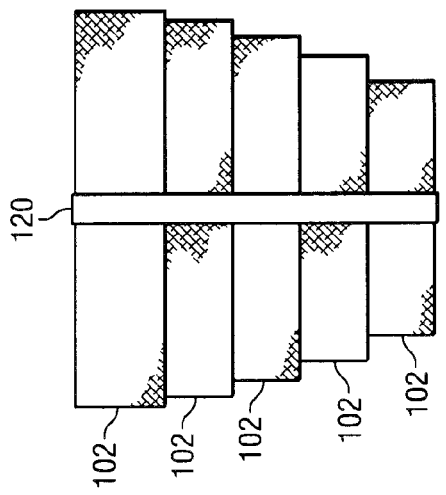
Figure 14A:
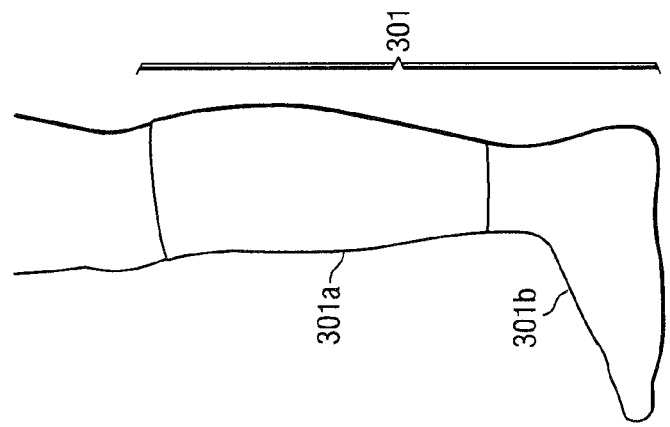

FIGS. 14a-c show an exemplary garment 300 employing the liner or sleeve 301 with a system of bands 102 connected by a spine 120. An exemplary sleeve 301 is shown in FIG. 14a, exemplary bands 102 are shown in FIG. 14b, and the combination of the sleeve 301 and bands 102 are shown together in FIG. 14c. The exemplary sleeve 301 includes the higher compression region 301b and the lower compression region 301a, but here, the transition between the regions is shown as a line, rather than with the optional wider transition zone 301c, as was described above with reference to FIG. 13.

FIG. 14b includes a series of bands 102 connected by the spine 120 in a manner described above. One or more bands 102 may have a length or width that varies from a length or width of other bands 102. Varying the length or width of the bands 102 may provide desired therapeutic compression characteristics, as described above. Also, although shown as partially overlapping in FIG. 14b, as described above, the bands 102 may lie directly adjacent each other or may be spaced, as desired to achieve the desired therapeutic compression characteristics. The spine 120 may operate as described above to secure the bands 102 together for convenience and to ensure proper spacing. As shown in FIGS. 12c and 12d, a spine 120 also may be used whether the bands 102 are removably attached or fixedly attached to the sleeve 301. In some embodiments, the spine 120 is the fastener that connects the bands 102 to the sleeve 301. As described above, the bands 102 may be short-stretch or other material, including non-elastic material.

FIG. 14c shows the bands 102 in place about the sleeve 301 on a patient's limb. The high compression area 301b cooperates with the bands 102 to provide the desired therapeutic compression.

Figure 15A:
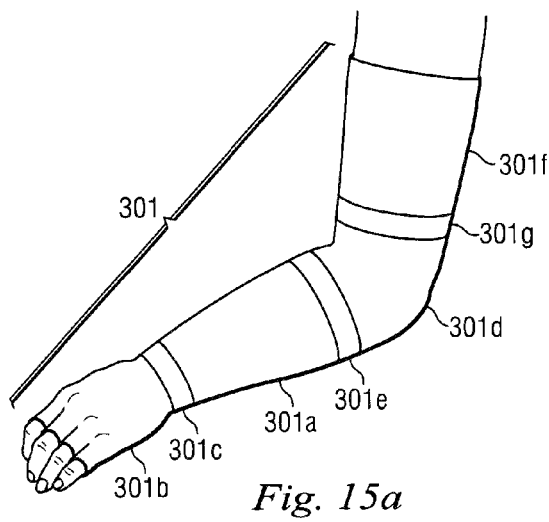
FIG. 15a is an illustration of an exemplary sleeve usable on an arm of a patient according to an embodiment of the present invention.

FIGS. 15a and 15b show additional exemplary embodiments of the hybrid sleeve 301. In FIG. 15a, the sleeve 301 is for a patient's arm and hand, while in FIG. 15b, the sleeve 301 is for a thigh, and may be used as a thigh high garment. Referring to both FIGS. 15a and 15b, in these two exemplary embodiments, the sleeve 301 includes a high compression region 301b distally on the hand in FIG. 15a or on the foot in FIG. 15b. This region 301b in FIG. 15a may be, for example, a hand-covering portion such as a glove, a half-finger glove, or a gauntlet, as is known in the art. The sleeve 301 also may include a lower therapeutic compression region 301a which, in some exemplary embodiments, may be covered by bands 102 (not shown in FIGS. 15a and 15b).

In some embodiments, and as shown in FIGS. 15a, and 15b, the sleeve 301 may include a region of higher therapeutic compression 301d around the elbow joint in FIG. 15a or around the knee joint in FIG. 15b. This may be desired in some embodiments, because it is difficult to engineer a short-stretch or non-elastic band to control edema over a joint, while not limiting comfort and range of motion. This is because the short-stretch or non-elastic bands 102 are designed to have limited stretch, and the joint area often requires more elasticity for the garment to be form fitting. It may be desired, therefore, that the joint area be free of bands 102 or other compression joint piece. Instead, the sleeve 301 may provide compression to the elbow area or knee area by itself, or alternatively, the higher compression region 301d may cooperate with the band(s) 102 or some other joint piece to provide therapeutic compression to the joint area to supplement the compression from the bands 102 or other joint piece.

Region 301f in FIGS. 15a and 15b is another region of lower therapeutic compression, and may have the same compression as region 301a. In these embodiments, the region 301f is disposed over the patient's upper arm in FIG. 15a and over the patient's thigh in FIG. 15b. Regions 301c, 301e, and 301g are optional transition regions which may provide graduated compression from the higher to lower compression regions.

In embodiments where the band 102 is formed of a short-stretch material, it is understood the short-stretch bands have stretch in the range of 15-100%. But, it is also understood that an elastic band with range of 0-300% may be used as a solution. These bands 102 may be sewn to the hybrid sleeve 301, may be selectively attachable by hook and loop fasteners, buttons, snaps, or the like, or may be sewn, welded, or otherwise attached to the sleeve 301. In addition, the bands 102 may or may not be connected to the spine 120, as described above.

Figure 16:
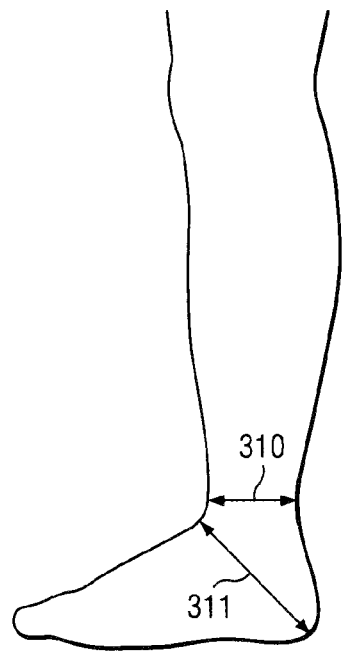
FIG. 16 is an illustration of a typical leg and foot.

The garment 300, including the sleeve 301, may be easier to don and doff than conventional compression stockings for any of several reasons. First, the mainstay of conventional compression stockings is that the maximal compression should be in the ankle area. The ankle area is also the smallest limb circumference in most individuals, as indicated in FIG. 16, showing a typical leg and ankle area. An ankle circumference, represented by the reference numeral 310, is the least ankle circumference, while a circumference from the anterior ankle to the apex of the heel, represented by the reference numeral 311, is much greater. The ankle-heel circumference 311 is in almost all people, much larger than the least ankle circumference 310 and may be a ratio of 1.2-2.5 times larger than the least ankle circumference 310. For example, in the case of the author, the least ankle circumference is 24 cm and the circumference from the anterior ankle to the heel apex is 33.5 cm, a ratio of 1.4. The significance of this is that conventional compression stockings are often designed to apply the greatest compression to the ankle area, and therefore must be created with the smallest ankle circumference. Yet in order to don such a garment, the portion of the garment with the smallest circumference and greatest compression must be dragged past the heel apex, making the garment difficult to don.

Furthermore, in order to don a compression stocking, the patient must not only reach the toes, but pull the compression stocking open and pull it up and over the toes in the donning process. This is difficult for patients with weak hand strength, bad backs, big bellies, pain in the abdominal area (for example after surgery) or poor pulmonary function.

Thus it is highly desirable to create a compression garment which maximally augments the calf muscle function and lymphangion micropump action to improve lymphatic and venous return, and in addition, includes highly desirable qualities of being easier to don around the back of the heel, and requires overall less hand strength to don and doff.

Figure 17:
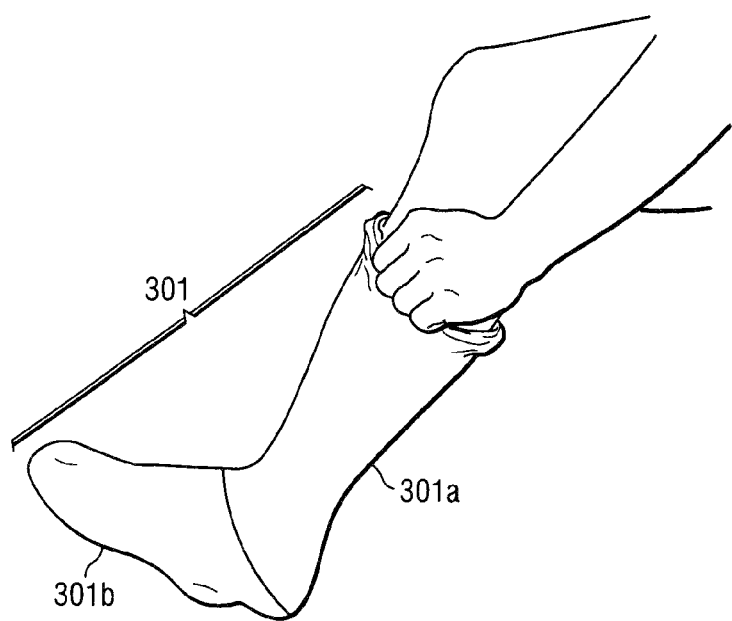
FIG. 17 is an illustration of an exemplary sleeve being placed on a patient.

One reason why the hybrid liner may be easier to don than conventional compression stockings is discussed with reference to FIG. 17. For this example, we will assume the distal region 301b has 20 mm compression and the proximal region 301a has 2 mm compression. The proximal region 301a of the sleeve 301 slips on like a loose sock until the patient starts to pull the distal portion 301b of the garment sleeve 301 onto the foot. As the distal region 301b of the garment sleeve 301 is pulled around the back of the heel, we will stop time and examine the garment sleeve 301 just as the transition between 301a and 301b spans the circumferential distance between the anterior ankle and the heel apex (shown as 311 in FIG. 16). If we stop and examine the compression level along this transition line at circumference 311, we see that there is 2 mm compression proximal to circumference line 311 and 20 mm distal to circumference line 311. Along circumference line 311 therefore, the compression will be the average of 2 mm and 20 mm (discounting additional compression from the increased stretch along this girth), which averages 11 mm. The patient thus can 'pop' the higher compression region up and over the back of the heel for easier and quicker donning, so that it fits as shown in FIG. 14a. In contrast, if we tried to don a 20 mm conventional compression stocking, the average compression along this same line would be greater than 20 mm. Thus, donning the hybrid sleeve 301 requires significantly less strength to don. Furthermore, the patient may don the higher compression region 301b with less back flexion while holding the hybrid sleeve further proximally, which makes it easier to don.

One factor that contributes to reducing the strength required to don the sleeve 301 is the location of the transition line relative to the ankle area on the patient. In the exemplary embodiment described, the transition line is configured to lie proximal of but adjacent to the ankle area, as shown in FIG. 14a. Thus, the ankle area is provided with a desired level of therapeutic compression from the higher compression region 301b, but the transition from the lower compression area 301a may ease the difficulty of donning the liner 301 over the anterior ankle and the heel apex at the circumference line 311. It should be noted that in some exemplary embodiments, the transition line or transition region may overlay a portion of the ankle area or may be further proximal of the ankle area.

The bands 102, applied over the sleeve 301 as described above, may provide additional therapeutic compression to the low compression region 301a, and may even provide better calf muscle augmentation of venous return than a conventional 40 mm compression garment. Thus the invention may be simultaneously easier to don and may provide superior results compared to conventional compression garments such as stockings.

In the case of surgical patients, such as knee and hip replacement patients, it is desirable to create a garment to control post-operative edema formation in the limb. This garment is important to be designed such that one can access the knee area to examine the incision. Furthermore, it may be desirable to have the knee and thigh portion of the garment separate from the leg and ankle portions, so that they can be discontinued or selectively removed. For example, in knee surgery patients, it may be desirable to wear the entire thigh-high garment for the first 10 days post-operatively. After this time period, it may be that the thigh portion is no longer needed and can be removed, and the foot and leg portion can be worn an additional period of time such as an additional 10-20 days. This is often needed in order to prevent edema reformation in this distal portion of the limb, until a time at which the entire garment is no longer necessary. Control of edema during the post-op period can prevent long term complications such as chronic edema. This type of garment may also have important use in saphenous vein harvest in cardiovascular bypass surgery and many other types of surgery such as knee arthroscopy and repair and other orthopaedic and podiatric surgeries, as well as in vein surgery.

Figure 19:
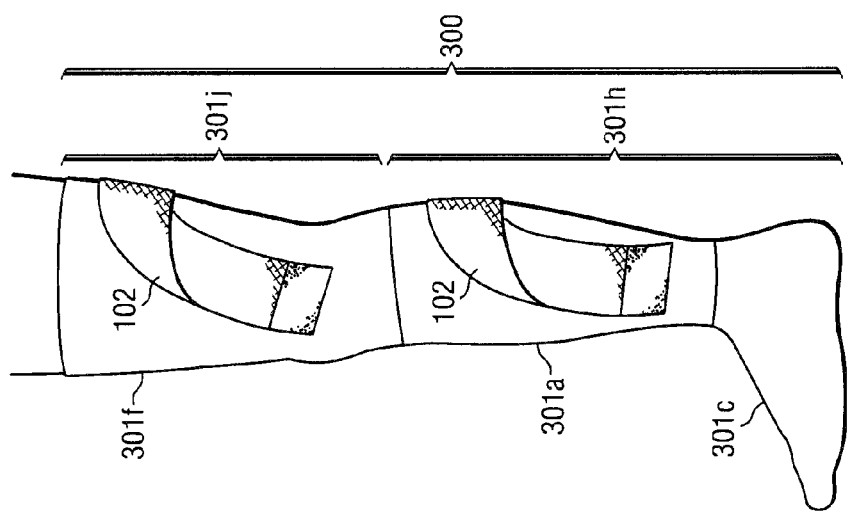
FIG. 19 is an illustration of an exemplary garment having two sleeves.
Figure 18:
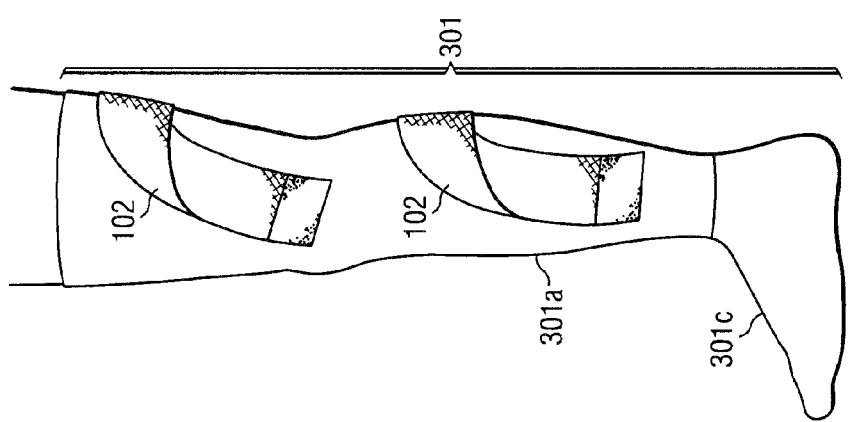
FIG. 18 is an illustration of an exemplary garment having a thigh-high sleeve.

In one aspect, shown in FIG. 18, this garment, referenced by the numeral 300, comprises a sleeve 301 or stocking with a first compression area 301c from the ankle area distally including the foot, and a second compression area 301a proximal to the ankle area. We will call this sleeve a hybrid liner, and it will function like a compression stocking from the ankle distally. From the ankle proximally, it will be more similar to a liner. This garment 300 further comprises one set of elastic, short-stretch, or inelastic bands 102 to apply therapeutic compression to the ankle and calf areas, and a second set of elastic or inelastic bands 102 to apply compression to the thigh and knee areas. The liner may be selectively detachable, separate, or permanently attached to this hybrid liner. In some embodiments, as shown in FIG. 19, the garment 300 is configured with a calf sleeve 301h and a thigh and knee sleeve 301j, such that the thigh and knee portion 301j of the garment 300 may be removed separate from the rest of the garment 300. As shown, this garment 300 may contain a second liner to extend around the knee and thigh area, separate from the portion that covers the foot, ankle, and calf areas.

Figure 20:
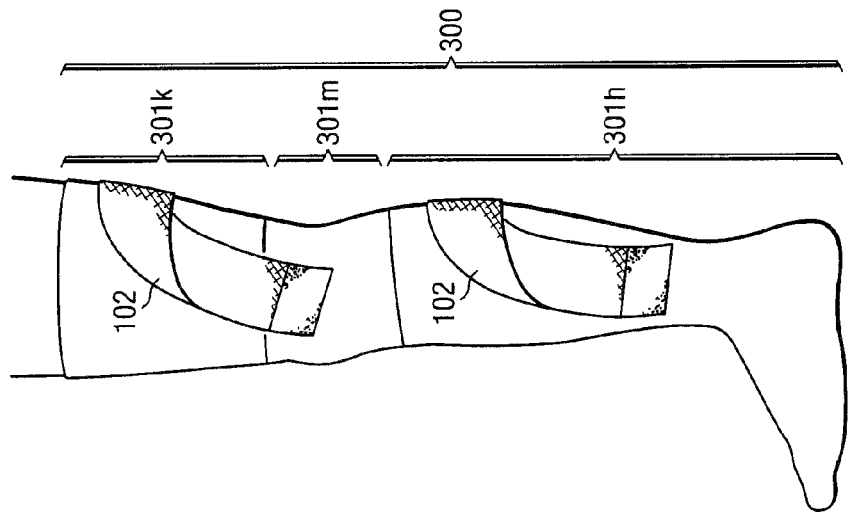
FIG. 20 is an illustration of an exemplary garment having three sleeves.

In another aspect, an example of which is shown in FIG. 20, a garment 300 comprises a footpiece and leg wrap sleeve 301h to apply compression to the foot and ankle and calf areas, a separate thigh wrap sleeve 301k to apply compression to the thigh area, and a separate knee wrap 301m. Here the knee wrap 301m may be formed as a sleeve or as a band, of elastic, inelastic, or short-stretch elastic material to apply compression selectively to the knee and connect the thigh piece and knee piece. This wrap 301m may be attached to the leg or thigh-wrap or be separate with hook and loop or other attachment mechanism at either end. The knee piece 301m can be selectively removed to examine the knee area without disturbing the rest of the garment. Alternatively, the garment 300 may include a knee piece which connects the thigh wrap and the knee wrap. The knee piece may be permanently attached to the knee wrap or the thigh wrap, or may be selectively detachable.

Figure 21:
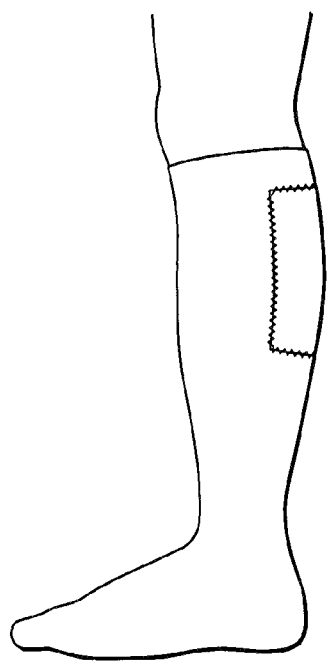
FIG. 21 is an illustration of an exemplary sleeve having calf area reinforcement.

In another exemplary embodiment, there is a compression stocking or sleeve with modified components in order to better augment venous flow during calf muscle augmentation. In one aspect, the modified components include a compression stocking with less elasticity in the calf area. This could be a knee-high or thigh-high compression stocking as described in the embodiments above. There are many ways to accomplish this. One way is to simply sew a rectangular piece of non-elastic or less-elastic material into the posterior aspect of the calf, as is shown in FIG. 21. Another way create less elasticity in the calf region is to use less elastic yarns in the calf portion of the garment. Yet another way to achieve less elasticity in the calf area is to vary the weave of the stocking. The importance of this invention is that less elasticity in the calf area means there is more augmentation of the calf muscle pump with calf muscle activation. Therefore, this invention would mainly be of benefit in active wearers, or in wearers who did exercises such as foot movements which would activate the calf muscle.

Another aspect of this invention is to make a sleeve for the leg out of compression fabric such as high performance compression Lycra type of material. By using extra material sewn into the calf portion, either rectangular patch or an extra sleeve portion, the wearer would have less elasticity in the calf area. In one aspect, the bias of the material is altered to create several versions of the product, so that the size of the rectangular, the material chosen, and the bias area all considered along with the calf diameter in order to maximize the augmentation of the calf muscle pump.

Figure 22:
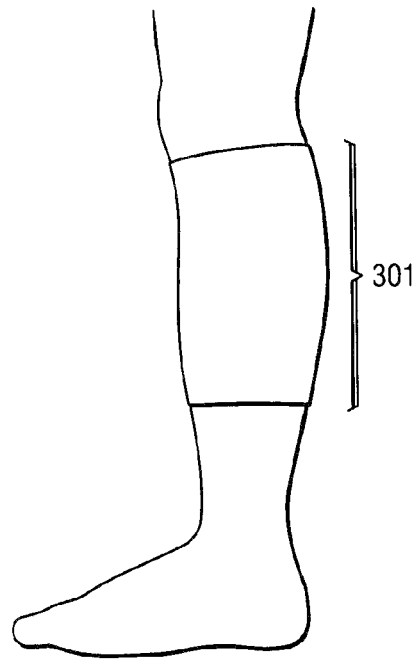
FIG. 22 is an illustration of an exemplary sleeve for the calf area.

Another aspect of this invention is to forgo a sleeve covering the entire limb, and create a form-fitting garment that will fit around the calf area and can be worn alone or bare while exercising in order to decrease limb edema. One example of such a sleeve is shown in FIG. 22 and referenced by the numeral 301. The sleeve 301 may include a proximal end having an opening sized to fit around an upper calf area on the patient's leg and a distal end having an opening sized to fit around a lower calf area on the patient's leg. A body portion extends between the proximal and distal ends and may be configured to provide therapeutic compression to the calf area. In some embodiments, the sleeve 301 may be used with bands, as described herein, to further adjust the compression level at the calf area.

Figure 23:
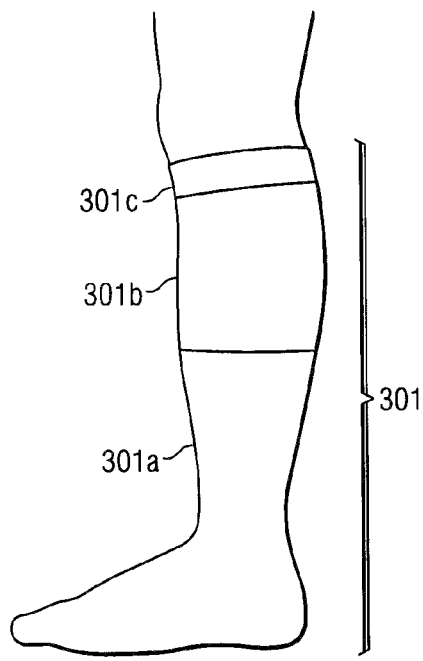
FIG. 23 is an illustration of an exemplary sleeve having compression in the calf area.

FIG. 23 shows an additional embodiment of a sleeve 301 configured to provide therapeutic compression to the calf area of a limb. In this embodiment, the sleeve 301 includes a first higher compression area 301b disposed to extend about a calf area of the limb. It may extend circumferentially about the calf area or alternatively, less than completely circumferentially around the calf area. The sleeve 301 also includes a second lower compression area 301a disposed distally of the higher compression area 301b, and in some embodiments, a third lower compression area 301c disposed proximal the higher compression region. Here, the lower compression area 301a extends on the limb below the calf area, and in the exemplary embodiment shown, covers the ankle area and the foot area. In other embodiments, the sleeve 301 may cover only the ankle area and the calf area, with the calf area having a higher compression. In some exemplary embodiments, the higher compression area 301b has a compression greater than the lower compression area 301a by about 5 mm or more.

In the embodiment of FIG. 23, and in other embodiments disclosed herein, the higher compression area 301b may be formed by using less elastic weave in the sleeve region intended to cover the calf area. By reducing the elasticity, the higher compression region 301b may more tightly fit around the calf area. Accordingly, the higher compression region 301b may have a first elastomeric stretch that is less than the elastomeric stretch of the and the second lower compression region 301a. Thus, the reinforced elastomeric compression sleeve 301 may augment compression to the calf area and improves venous return.

In all aspects of this invention, it is anticipated that the design of the garment is such that, while it is providing increased compression to the calf muscle while activated, the garment is designed such that it will reduce edema distal to the calf area, instead of acting like a tourniquet and blocking lymphatic and venous flow distal to the calf area.

In one exemplary aspect, this disclosure is directed to a sleeve for providing compression force to a limb. The sleeve may include a proximal end and a distal end, the proximal end having an opening for receiving the limb. A first region may be configured to provide a first level of therapeutic compression greater than 5 mm. A second region may be configured to extend along the limb from the first region, the second region being configured to provide a second level of compression less than the first level of therapeutic compression.

In one aspect, the first level of therapeutic compression is greater than 8 mm.

In one aspect, the sleeve is in the form of a knee high stocking sized to fit over a patient's ankle area and calf muscle, and wherein the first region is configured to provide the therapeutic compression to the ankle and foot area.

In one aspect, the sleeve further comprises a transition line between the first region and the second region, the transition line being disposed so that it lies adjacent the ankle area.

In one aspect, the transition line is part of a transition zone having a third level of compression, the third level of compression being greater than the second level and less than the first level of compression.

In one aspect, the sleeve is sized to fit over a patient's wrist area and forearm, and wherein the first region is configured to provide the therapeutic compression to the wrist and hand area.

In one aspect, the sleeve includes a transition line between the first region and the second region, the transition line being disposed so that it lies adjacent the wrist area.

In one aspect, the transition line is part of a transition zone having a third level of compression, the third level of compression being greater than the second level and less than the first level of compression.

In one aspect, the sleeve includes a third region formed as a band adjacent the second region, the third region being configured to provide a third level of therapeutic compression greater than 5 mm.

In one aspect, the sleeve is in the form of a thigh-high stocking or panty hose stocking sized to fit over a patient's ankle area and knee joint, and wherein the first region is configured to provide the first level of therapeutic compression to the ankle area, and the third region is configured to provide the third level of therapeutic compression to the knee joint.

In one aspect, the sleeve is sized to further fit over a portion of a thigh of a patient, the sleeve including a fourth region located to fit over a thigh portion of the patient, the fourth region being configured to provide a fourth level of compression different than the third level of therapeutic compression.

In one aspect, the sleeve is sized to fit over a patient's wrist and hand area and elbow area, and wherein the first region is configured to provide the first level of therapeutic compression to the wrist area of the patient, and the third region is configured to provide the third level of therapeutic compression greater than 5 mm to the elbow area.

In one aspect, the third region is configured to provide the third level of therapeutic compression greater than 5 mm to the elbow area.

In one aspect, the sleeve is sized to further fit over a portion of an upper arm of a patient, the sleeve including a fourth region located to fit over an upper arm portion of the patient, the fourth region being configured to provide a fourth level of compression less than the third level of therapeutic compression.

In one aspect, the sleeve comprises a hand-covering portion forming the distal end, the hand-covering portion being at least a portion of the first region.

In one aspect, the second level of compression is between 0 and 40 mm.

In one aspect, the first level of therapeutic compression is greater than 15 mm.

In one aspect, the first level of therapeutic compression is greater than 30 mm.

In one aspect, the first region is formed of a short-stretch, elastic, or inelastic material.

In one aspect, the first region is formed of a short-stretch material.

In another exemplary aspect, this disclosure is directed to a garment for providing compressive force to a limb, the garment may comprise a sleeve including a proximal end and a distal end, the proximal end having an opening for receiving the limb. The garment also may comprise a compression band attached to the sleeve and configured to extend about a first portion of the sleeve and configured to impart a therapeutic compression to the limb.

In one aspect, the compression band is formed of one of a short-stretch material and an inelastic material.

In one aspect, the compression band comprises a short-stretch band having a dynamic compression characteristic and a maximum stretch characteristic so that when the band is at the maximum stretch and wrapped around the respective sleeve portion, the band provides a predetermined level of compression.

In one aspect, the compression band is a first compression band, the garment further including a second compression band attached to the sleeve and configured to wrap around a second portion of the sleeve.

In one aspect, the first and second compression bands are disposed to overlap.

In one aspect, the sleeve is configured to extend about a leg of a patient and the first and second compression bands are sized to extend about a calf muscle of the leg. Some embodiments include additional compression bands that extend about a calf muscle of the leg or about other portions of the leg.

In one aspect, the first and second compression bands are configured to provide different levels of compression to the sleeve.

In one aspect, a width of the first compression band differs from a width of the second compression band.

In one aspect, the compression band is attached to the sleeve using by one of: a hook and loop fastener, a snap, and a button.

In one aspect, the compression band is attached to the sleeve by a spine.

In one aspect, the compression band is configured to impart a therapeutic compression load greater than 5 mm.

In one aspect, the sleeve comprises a first region configured to provide a first level of therapeutic compression; and a second region configured to extend along the limb from the first region, the second region being configured to provide a second level of compression less than the first level of therapeutic compression.

In another exemplary aspect, this disclosure is directed to a garment for providing compressive force to a limb. The garment may comprise a sleeve including a proximal end and a distal end, the proximal end having an opening for receiving the limb, the sleeve having a first region configured to provide a first level of therapeutic compression and having a second region configured to extend from the first region and being configured to provide a second level of compression less than the first level of therapeutic compression. The garment also may comprise a compression band configured to extend about a first portion of the sleeve and configured to impart a therapeutic compression to the limb.

In one aspect, the compression band is formed of one of a short-stretch material and an inelastic material.

In one aspect, the compression band comprises a short-stretch band having a dynamic compression characteristic and a maximum stretch characteristic so that when the band is at the maximum stretch and wrapped around the respective sleeve portion, the band provides a predetermined level of compression.

In one aspect, the compression band is a first compression band, the garment further including a second compression band attached to the sleeve and configured to wrap around a second portion of the sleeve.

In one aspect, the first and second compression bands are disposed to overlap.

In one aspect, the sleeve is configured to extend about a leg of a patient and the first and second compression bands are sized to extend about a calf muscle of the leg.

In one aspect, the first and second compression bands are configured to provide different levels of compression to the sleeve.

In one aspect, a width of the first compression band differs from a width of the second compression band.

In one aspect, the compression band is attached to the sleeve using by one of: a hook and loop fastener, a snap, and a button.

In one aspect, the compression band is attached to the sleeve by a spine.

In another exemplary aspect, the present disclosure is directed to a method of treating an elevated concentration of interstitial fluid in a body area of a patient. The method may comprise diagnosing a condition of interstitial fluid in a body area and determining an appropriate sleeve size to cover the body area. It also may comprise prescribing a garment for providing compressive force to a limb. The garment may include a proximal end and a distal end, the proximal end having an opening for receiving the limb and a first region configured to provide a first level of therapeutic compression greater than 5 mm. The garment also may include a second region configured to extend along the limb from the first region, the second region being configured to provide a second level of compression less than the first level of therapeutic compression.

The foregoing has outlined features of several embodiments according to aspects of the present invention. Those skilled in the art should appreciate that they may readily use the present disclosure as a basis for designing or modifying other processes and structures for carrying out the same purposes and/or achieving the same advantages of the embodiments introduced herein. For example, many of the above-described embodiments are described with a more expensive material. In other embodiments, the garments can be constructed of single-use or disposable materials. Furthermore, features of the garments can be made to ensure that the garments are not improperly reused, such as having adhesives or portions of the garment that rapidly deteriorate in response to some predetermined condition such as the elapse of time or a high-temperature cleaning operation. Furthermore, some of the embodiments above are illustrated as being used with an ankle, a lower leg, a knee, a thigh, an arm and so forth. It is understood that the present embodiments apply generally to any limb or joint which may benefit from therapeutic compression. Those skilled in the art should also realize that such equivalent constructions do not depart from the spirit and scope of the present disclosure, and that they may make various changes, substitutions and alterations herein without departing from the spirit and scope of the present disclosure.

What is claimed is:

1. A compression garment comprising:
   first and second bands, each comprising a first end, second end opposite the first end, and an intermediate portion located between the first and second ends;
   the first band wrapping around a first portion of a limb;
   the second band wrapping around a second portion of the limb;
   the first and second bands positioned such that the intermediate portion of the first band and the intermediate portion of the second band abut without overlapping one another;
   the first and second bands comprising short-stretch material having a maximum elastic elongation in the range of about 15% up to about 100%; and
   the first and second bands, each applying, to the limb, a level of compression selected from the group consisting of 8-15 mm Hg, 15-20 mm Hg, 20-30 mm Hg, 30-40 mm Hg, and greater than 40 mm Hg.

2. The garment of claim 1, wherein the first band is connected to the second band in a permanent manner.

3. The garment of claim 2, wherein the first and second bands are connected to one another in a seamless manner.

4. The garment of claim 2, wherein the first end of the first band overlaps and engages the second end of the first band to maintain the first band wrapped around the first portion of the limb.

5. The garment of claim 4, wherein the first end of the second band overlaps and engages the second end of the second band to maintain the second band wrapped around the second portion of the limb.

6. The garment of claim 5, wherein the intermediate portion of the first band is seamlessly connected to the intermediate portion of the second band.

7. The garment of claim 1, wherein the intermediate portion of the first band is seamlessly connected to the intermediate portion of the second band.

8. The garment of claim 1, wherein:
   the first end of the first band comprises a tab of the short stretch material extending from the intermediate portion of the first band to overlap the second end of the first band; and
   the first end of the second band comprises a tab of the short stretch material extending from the intermediate portion of the second band to overlap the second end of the second band.

9. The garment of claim 8, wherein at least a portion of the first end of the first band overlaps at least a portion of the second band.

10. The garment of claim 1, wherein the first and second bands comprise short-stretch material having a maximum elastic elongation in the range of about 30% up to about 50%.

11. The garment of claim 1, further comprising a patch of non-elastic or less elastic material positioned to cover at least a portion of a calf muscle of the limb.

12. A compression garment comprising:
    a sheet of short stretch material having a maximum elastic elongation in the range of about 15% up to about 100%;
    the sheet comprising
       first and second bands, each comprising a first end, a second end opposite the first end, and an intermediate portion located between the first and second ends, the first end comprising a tab extending from the intermediate portion, and
       the first and second bands positioned such that the intermediate portion of the first band and the intermediate portion of the second band abut without overlapping one another; and
    first and second engagement mechanisms, each connected to the sheet on the tab of a respective band of the first and second bands.

13. The garment of claim 12, wherein the intermediate portion of the first band is seamlessly connected to the intermediate portion of the second band.

14. The garment of claim 13, wherein:
    the first band wraps circumferentially around a first portion of a limb; and
    the second band wraps circumferentially around a second portion of the limb.

15. The garment of claim 14, wherein:
    the first engagement mechanism secures the first end of the first band in a position overlapping the second end of the first band; and
    the second engagement mechanism secures the first end of the second band in a position overlapping the second end of the second band.

16. The garment of claim 15, wherein the first and second bands each apply, to the limb, a level of compression selected from the group consisting of 8-15 mm Hg, 15-20 mm Hg, 20-30 mm Hg, 30-40 mm Hg, and greater than 40 mm Hg.

17. A method of compression therapy, the method comprising:
    obtaining a compression garment comprising a sheet of short stretch material having a maximum elastic elongation in the range of about 15% up to about 100%, the sheet comprising
       first and second bands, each comprising a first end, a second end opposite the first end, and an intermediate portion located between the first and second ends, the first end comprising a tab extending from the intermediate portion, and
       the first and second bands positioned such that the intermediate portion of the first band and the intermediate portion of the second band abut without overlapping one another;
    applying the compression garment to a limb of a patient suffering from venous valvular insufficiency, postphlebitic syndrome, lymphedema, vein-harvest recovery, or vein-surgery recovery;
    delivering, by the first band to a first portion of the limb after the applying, a first level of compression selected from the group consisting of 8-15 mm Hg, 15-20 mm Hg, 20-30 mm Hg, 30-40 mm Hg, and greater than 40 mm Hg; and
    delivering, by the second band to a second portion of the limb after the applying, a second level of compression selected from the group consisting of 8-15 mm Hg, 15-20 mm Hg, 20-30 mm Hg, 30-40 mm Hg, and greater than 40 mm Hg.

18. The method of claim 17, wherein the compression garment further comprises a sleeve.

19. The method of claim 18, wherein the sleeve is formed by material connected to the first and second bands.

20. The method of claim 19, wherein the applying comprises:
- sliding the limb into the sleeve;
- wrapping the first band circumferentially around the first portion of the limb;
- securing, with a first engagement mechanism, the first end of the first band in a position overlapping the second end of the first band;
- wrapping the second band circumferentially around the second portion of the limb; and
- securing, with a second engagement mechanism, the first end of the second band in a position overlapping the second end of the second band.

\* \* \* \* \*